US008980896B2

(12) United States Patent
Holmes et al.

(10) Patent No.: US 8,980,896 B2
(45) Date of Patent: Mar. 17, 2015

(54) COMPOSITIONS COMPRISING MACROCYCLIC LACTONE COMPOUNDS AND SPIRODIOXEPINOINDOLES

(75) Inventors: Robert Holmes, Auckland (NZ); Majid Razzak, Glenfiled (NZ)

(73) Assignee: Merial, Inc., Duluth, GA (US)

( * ) Notice: Subject to any disclaimer, the term of this patent is extended or adjusted under 35 U.S.C. 154(b) by 22 days.

(21) Appl. No.: 12/970,684

(22) Filed: Dec. 16, 2010

(65) Prior Publication Data

US 2011/0160218 A1    Jun. 30, 2011

Related U.S. Application Data

(60) Provisional application No. 61/287,532, filed on Dec. 17, 2009.

(51) Int. Cl.
| | | |
|---|---|---|
| *A01N 43/58* | (2006.01) | |
| *A01N 43/60* | (2006.01) | |
| *A61K 31/50* | (2006.01) | |
| *A61K 31/495* | (2006.01) | |
| *A01N 43/40* | (2006.01) | |
| *A61K 31/44* | (2006.01) | |
| *A01N 43/02* | (2006.01) | |
| *A61K 31/335* | (2006.01) | |
| *C07D 471/04* | (2006.01) | |
| *A61K 31/365* | (2006.01) | |

(52) U.S. Cl.
CPC ............ *C07D 471/04* (2013.01); *A61K 31/365* (2013.01); *A61K 31/495* (2013.01)
USPC ............................. 514/250; 514/341; 514/450

(58) Field of Classification Search
CPC .............. A61K 31/365; A61K 31/495; A61K 2300/00; C07D 471/04
USPC ........................... 424/400; 514/250, 341, 450
See application file for complete search history.

(56) References Cited

U.S. PATENT DOCUMENTS

| | | | | |
|---|---|---|---|---|
| 3,950,360 | A | 4/1976 | Aoki et al. | 260/343.2 |
| 4,199,569 | A | 4/1980 | Chabala et al. | 424/180 |
| 4,866,060 | A | 9/1989 | Mrozik | 514/250 |
| 4,874,749 | A | 10/1989 | Mrozik et al. | 514/30 |
| 4,923,867 | A | 5/1990 | Blizzard et al. | 514/250 |
| 5,277,912 | A * | 1/1994 | Lowe et al. | 424/438 |
| 5,703,078 | A | 12/1997 | Lee et al. | 514/250 |
| 5,750,695 | A | 5/1998 | Lee et al. | 544/341 |
| 6,426,333 | B1 | 7/2002 | Huet et al. | 514/30 |
| 6,482,425 | B1 | 11/2002 | Huet et al. | 424/406 |
| 6,962,713 | B2 | 11/2005 | Huet et al. | 424/405 |
| 6,998,131 | B2 | 2/2006 | Soll et al. | 424/406 |
| 2002/0037863 | A1 * | 3/2002 | Geary | 514/28 |
| 2003/0055089 | A1 * | 3/2003 | Sirinyan et al. | 514/341 |
| 2005/0064032 | A1 * | 3/2005 | Lowe et al. | 424/468 |
| 2007/0293446 | A1 * | 12/2007 | Soll et al. | 514/27 |
| 2009/0036458 | A1 * | 2/2009 | Fattohi et al. | 514/250 |

FOREIGN PATENT DOCUMENTS

| | | | | |
|---|---|---|---|---|
| EP | 0390532 | A2 | 10/1990 | ........... C07D 491/22 |
| EP | 717993 | B1 * | 3/2000 | |
| WO | WO 91/09961 | A2 | 7/1991 | ........... C07D 491/22 |
| WO | WO 92/00300 | A2 | 1/1992 | ........... C07D 491/22 |
| WO | WO 92/22555 | A1 | 12/1992 | ........... C07D 491/22 |
| WO | WO 97/03988 | A1 | 2/1997 | ........... C07D 491/22 |
| WO | WO 01/76370 | A2 | 10/2001 | ............. A01N 43/90 |
| WO | WO 2008/136791 | A1 | 11/2008 | ........... C07D 493/10 |
| WO | WO 2009/004432 | A1 | 1/2009 | ........... A61K 31/365 |

OTHER PUBLICATIONS

Swanson et al (2012). "Albendazole Therapy and Enteric Parasites in United States-Bound Refugees." The New England Journal of Medicine, 366(16): 1498-1507.*
"The Structure of Paraherquamide, a Toxic Metabolite from *Penicillum paraherquei*," Yamazaki et al., *Tetrahedron Letters*, 1981, 22, 135-136.
"Structures of Macfortines B and C (X-Ray Analysis), Alkaloids from *Penicillum roqueforti*," Prange et al., *Tetrahedron Letters*, 1981, 22, 1977-1980.
"Avermectin/Milbemycin Resistance in Trichostrongyloid Nematodes," Gill et al., *International Journal for Parasitology*, 1998, 28, 863-877.
"Novel Antinematodal and Antiparasitic Agents from *Penicillum charlesii*," Liesch et al., *The Journal of Antibiotics*, 1990, 43(11), 1380-1386.
"New Paraherquamide Antibiotics with Anthelmintic Activity," Blanchflower et al., *The Journal of Antibiotics*, 1991, 44(5), 492-497.
"Isolation and Structure (X-Ray Analysis) of Marcfortine A, a New Alkaloid from *Penicillium roqueforti*," *Journal of the Chemical Society—Chemical Communications*, 1980, 601-602.

* cited by examiner

*Primary Examiner* — Brian-Yong Kwon
*Assistant Examiner* — Doan Phan
(74) *Attorney, Agent, or Firm* — Judy Jarecki-Black; Peter Dolan; Merial, Inc.

(57) ABSTRACT

The present invention provides formulations which may comprise macrocyclic lactones and at least one spirodioxepinoindole derivative or a spirooxepinoindole derivative for combating parasites in birds and mammals. The invention also provides for an improved method for eradicating, controlling and preventing parasite infestation in birds and mammals.

19 Claims, No Drawings

US 8,980,896 B2

COMPOSITIONS COMPRISING MACROCYCLIC LACTONE COMPOUNDS AND SPIRODIOXEPINOINDOLES

CROSS REFERENCE TO RELATED APPLICATIONS

This application claims the benefit of priority to U.S. Provisional Patent Application No. 61/287,532 filed Dec. 17, 2009, which is incorporated herein by reference in its entirety.

FIELD OF THE INVENTION

This invention relates to novel anthelmintic compositions which may comprise at least one macrocyclic lactone derivative for combating parasites in birds and mammals. This invention also provides for novel anthelmintic compositions which may comprise at least one macro cyclic lactone derivative and at least one spirodioxepinoindole derivative or spirooxepinoindole derivative for combating parasites. This invention also provides for an improved method for eradicating, controlling, and preventing parasite infestation in birds and mammals.

BACKGROUND OF THE INVENTION

Animals, such as mammals and birds, are often susceptible to parasite infestations. These parasites may be ectoparasites, such as insects, and endoparasites such as filariae and worms. Domesticated animals, such as cats and dogs, are often infested with one or more of the following ectoparasites:

cat and dog fleas (*Ctenocephalides felis, Ctenocephalides* sp. and the like),
ticks (*Rhipicephalus* sp., *Ixodes* sp., *Dermacentor* sp., *Amblyoma* sp. and the like), and
mites (*Demodex* sp., *Sarcoptes* sp., *Otodectes* sp. and the like),
lice (*Trichodectes* sp., *Cheyletiella* sp., *Lignonathus* sp., and the like),
mosquitoes (*Aedes* sp., *Culex* sp., *Anopheles* sp., and the like) and
flies (*Hematobia* sp., *Musca* sp., *Stomoxys* sp., *Dermatobia* sp., *Coclyomia* sp., and the like).

Fleas are a particular problem because not only do they adversely affect the health of the animal or human, but they also cause a great deal of psychological stress. Moreover, fleas are also vectors of pathogenic agents in animals, such as dog tapeworm (*Dipylidium caninum*), and humans.

Similarly, ticks are also harmful to the physical and psychological health of the animal or human. However, the most serious problem associated with ticks is that they are the vector of pathogenic agents, agents which cause diseases in both humans and animal. Major diseases which are caused by ticks include borrelioses (Lyme disease caused by *Borrelia burgdorferi*), babesioses (or piroplasmoses caused by *Babesia* sp.) and rickettsioses (also known as Rocky Mountain spotted fever). Ticks also release toxins which cause inflammation or paralysis in the host. Occasionally, these toxins are fatal to the host.

Moreover, mites and lice are particularly difficult to combat since there are very few active substances which act on these parasites and they require frequent treatment.

Likewise, farm animals are also susceptible to parasite infestations. For example, cattle are affected by a large number of parasites. A parasite which is very prevalent among farm animals is a tick genus *Boophilus*, especially those of the species *microplus* (cattle tick), *decoloratus* and *anulatus*. Ticks, such as *Boophilus microplus*, are particularly difficult to control because they live in the pasture where the farm animals graze. Other important parasites of cattle and sheep are listed as follows in order of decreasing importance:

myiases such as *Dermatobia hominis* (known as Berne in Brazil) and *Cochlyomia hominivorax* (greenbottle); sheep myiases such as *Lucilia sericata, Lucilia cuprina* (known as blowfly strike in Australia, New Zealand and South Africa). These are flies whose larva constitutes the animal parasite;
flies proper, namely those whose adult constitutes the parasite, such as *Haematobia irritans* (horn fly);
lice such as *Linognathus vitulorum*, etc.; and
mites such as *Sarcoptes scabiei* and *Psoroptes ovis*.

The above list is not exhaustive and other ectoparasites are well known in the art to be harmful to animals and humans. These include, for example migrating dipterous larvae.

Animals and humans also suffer from endoparasitical infections including, for example, helminthiasis which is most frequently caused by a group of parasitic worms described as nematodes or roundworms. These parasites cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

Many insecticides exist in the art for treating parasites. These insecticides vary in their effectiveness to a particular parasite as well as their cost. However the results of treatment with these insecticides are not always satisfactory because of, for example, the development of resistance by the parasite to the therapeutic agent, as is the case, for example, with carbamates, organophosphorus compounds and pyrethroids. Moreover, there is at the present time no truly effective method for controlling both ticks and helminths and less still an effective way of controlling the set of parasites indicated above. Thus, there is a need in the art for more effective antiparasitic formulations for treatment and protection of animals, e.g. mammals, fish and birds, for a wide range of parasites. Moreover, there is a need in the art for antiparasitic formulations which are easy to use on any type of domestic animal, irrespective of its size and the nature of its coat and which do not need to be sprinkled over the entire body of the mammal, fish or bird.

A new family of insecticides based on 1-N-phenylpyrazoles is described in Patents EP-A-295,217 and EP-A-352,944, which are hereby incorporated by reference in their entirety. The compounds of the families defined in these patents are extremely active and one of these compounds, 1-[2,6-$Cl_2$-4-$CF_3$ phenyl]-3-CN-4-[SO—$CF_3$]-5-$NH_2$ pyrazole, or fipronil, is particularly effective, not only against crop parasites but also against ectoparasites of mammals and birds. Fipronil is particularly, but not exclusively, effective against fleas and ticks.

Endectocidal compounds, which exhibit a degree of activity against a wide range endoparasites, are known in the art. These compounds possess a macrocyclic lactone ring and are known in the art to be particularly effective against ectoparasites, including lice, blowflies, flies, mosquitoes, mites, migrating dipterous larvae, and ticks, as well as endoparasites, such as nematodes and roundworms. Compounds of this group include avermectins, milbemycins, and derivatives of these compounds, for example, ivermectin or emamectin. Such substances are described, for example, in U.S. Pat. Nos.

3,950,360; 4,199,569; 4,879,749; and 5,268,710, all of which are hereby incorporated by reference in their entirety.

The paraherquamide family of compounds compounds are known class of compounds that include a spirodioxepino indole core with activity against certain parasites (see *Tet. Lett.* 1981, 22, 135, *J. Antibiotics* 1990, 43, 1380, and *J. Antibiotics* 1991, 44, 492). In addition, the structurally related marcfortine family of compounds, such as marcfortines A-C, are also known (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. Nos. 5,703,078 and 5,750,695, all of which are hereby incorporated by reference in their entirety. Examples of marcfortine derivatives can be found, for example, in WO 92/22555, U.S. Pat. Nos. 4,866,060, 4,923,867, all of which are hereby incorporated by reference in their entirety. The syntheses of these and structurally similar compounds are also described therein.

Recent publications have reported that certain trichostrongyloid parasites resistant to macrocyclic lactones such as ivermectin have an increased susceptibility to spirodioxepinoindoles such as paraherquamide (see Gill JH and Lacey E, International Journal for Parasitology, volume 28, pages 863-877, 1998). The present invention includes various substituted marcfortines and paraherquamides which are useful as antiparasitic agents. WO 20011076370, which is incorporated herein by reference, describes compositions comprising certain macro cyclic lactones and one or more spirodioxepinoindoles compounds to treat or prevent parasitic diseases. WO 2009/004432, which is hereby incorporated by reference in its entirety, describes compositions comprising 2-desoxoparaherquamide and abamectin as well as methods for the treatment of parasitic infections with the compositions.

While it is known in the art that it is sometimes possible to combine various parasiticides in order to broaden the antiparasitical spectrum, it is not possible to predict, a priori, which combinations will work for a particular animal or disease state. For this reason, the results of various combinations are not always successful and there is a need in the art for more effective formulations which may be easily administered to the animal. The effectiveness of formulations comprising 1-N-phenylpyrazole derivatives and macrolide lactone anthelmintic or parasitic agents, such as avermectins, ivermectins and milbemycin, against an endoparasite or an ectoparasite in a specific host is especially difficult to predict because of the numerous and complex host-parasite interactions.

Patent application AU-A-16 427/95 very broadly mentions the combination of a substituted 1-N-pyrazole derivatives with an avermectin, ivermectin or moxidectin in a discussion involving among a very large number of insecticides or parasiticides of various types, including fipronil. However, this patent application does not provide specific guidance to the skilled artisan on how to formulate a 1-N-pyrazole derivative with an avermectin or milbemycin type compound, let alone how to formulate a spot-on composition comprising these compounds. Moreover, the application does not indicate which specific parasites are susceptible to what specific combination.

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention.

SUMMARY OF THE INVENTION

The invention provides for compositions for the treatment or prophylaxis of parasites of mammals and birds, and in particular, cats, dogs, horses, chickens, sheep and cattle with the aim of ridding these hosts of all the parasites commonly encountered by mammals and birds. The invention also provides for effective and long lasting destruction of ectoparasites, such as fleas, ticks, mites, e.g. itch mites, mosquitoes, flies and lice, and of endoparasites, nematodes, such as filariae, hookworms, whipworms and roundworms of the digestive tract of animals and humans.

In particular this invention provides for novel composition for the treatment or prophylaxis of parasite infestations in mammals or birds which may comprise:
(A) an effective amount of a spirodioxepinoindole derivative or a spirooxepinoindole derivative;
(B) an effective amount of at least one macrocyclic lactone derivative; and
(C) a pharmaceutically effective carrier.

The invention also provides for an easy method of treating parasitic infestations or for the prophylaxis of parasite infestations in mammals or birds which may comprise administering to said mammal or bird an effective amount of a formulation according to the present invention.

This invention also provides for compositions comprising a combination of at least one macrocyclic lactone derivative and a spirodioxepinoindole derivative or a spirooxepinoindole, which exhibit synergistic activity against parasites when compared to formulations which contain only one class of therapeutic agent.

The very high effectiveness of the method and of the composition/formulations according to the invention provides not only for a high instantaneous effectiveness but also for an effectiveness of very long duration after the treatment of the mammal or bird. The compositions/formulations also provide an alternative to other commercial antiparasitic formulations such as FRONTLINE® (fipronil) and K-9 ADVANTIX® (imidacloprid/permethrin) should a parasite develop a resistance to these formulations.

For the purpose of this invention the term "pharmaceutical" or "pharmaceutically" is intended to encompass treatment of animals, humans and birds.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

This invention provides for a composition for the treatment or prophylaxis of parasite infestation in birds or mammals which may comprise:
(A) a pharmaceutically effective amount of at least one macrocyclic lactone, or a pharmaceutically acceptable salt thereof;
(B) a pharmaceutically effective amount of at least one spirodioxepinoindole, or a pharmaceutically acceptable salt thereof; and
(C) a pharmaceutically acceptable carrier.

This invention also provides for a composition for the treatment or prophylaxis of parasite infestation in birds or mammals which may comprise:
(A) a pharmaceutically effective amount of at least one macrocyclic lactone, or a pharmaceutically acceptable salt thereof;
(B) a pharmaceutically effective amount of at least one spirooxepinoindole, or a pharmaceutically acceptable salt thereof; and
(C) a pharmaceutically acceptable carrier.

Also provided are uses and methods comprising the compositions of the invention for the prevention or treatment of a parasitic infestation in birds or mammals or for in the manufacture of a medicament for the prevention or treatment of a parasitic infestation in birds or mammals.

Macrolide anthelmintic compounds may be used for treating endo- and ectoparasite infections in mammals and birds. Compounds that belong to this class of macrocyclic lactones include, but are not limited to, the avermectin and milbemycin series of macrolides. These compounds are potent antiparasitic agents against a wide range of internal and external parasites. Avermectins and milbemycins share the same common 16-membered macrocyclic lactone ring; however, milbemycins do not possess the disaccharide substituent on the 13-position of the lactone ring. In addition to treating parasitic insects, avermectins and milbemycins are used to treat endoparasites, e.g., round worm infections, in warm-blooded animals.

The avermectins may be isolated from the fermentation broth of an avermectin producing strain of *Streptomyces avermitilis* and derivatives thereof. The production, isolation and structural determination of the avermectins are documented in Albers-Schonberg, et. al, *J. Am. Chem. Soc.* 1981, 103, 4216-4221 and references cited therein. The description of the morphological characteristics of the culture is described in U.S. Pat. No. 4,310,519. Naturally occurring milbemycins are described in Aoki et al., U.S. Pat. No. 3,950,360, which is hereby incorporated by reference in its entirety, as well as in the various references cited in "The Merck Index" 12$^{th}$ ed., S. Budavari, Ed., Merck & Co., Inc. Whitehouse Station, N.J. (1996).

The avermectin and milbemycin series of compounds either are natural products or are semi-synthetic derivatives. The natural product avermectins are disclosed in U.S. Pat. No. 4,310,519, and the 22,23-dihydro avermectin compounds are disclosed in U.S. Pat. No. 4,199,569, both of which are hereby incorporated by reference in their entirety. The synthesis of avermectins has been documented (*J. Am. Chem. Soc.* 1989, 111, 2967; *J. Am. Chem. Soc.* 1986, 108, 2776) and research on deconjugation and epimerization of avermectin derivatives is also described in Hanessian, et al (*J. Am. Chem. Soc.* 1987, 109, 7063) and Fraser-Reid, et al (*J. Am. Chem. Soc.* 1987, 109, 933). For a general discussion of avermectins, which includes a discussion of their uses in humans and animals, see "Ivermectin and Abamectin," W. C. Campbell, ed., Springer-Verlag, New York (1989). Examples of avermectins include, but are not limited to, abamectin, dimadectin, doramectin, emamectin, eprinomectin, ivermectin, latidectin, lepimectin, and selamectin.

The milbemycins are the aglycone derivatives of the avermectins, such as those described, for example in U.S. Pat. Nos. 4,144,352; 4,791,134; and 6,653,342, all of which are hereby incorporated by reference in their entirety. Particularly important anthelmintics of this family include moxidectin, as described, for example in U.S. Pat. Nos. 7,348,417; and 4,916,154 (and references cited therein), which are hereby incorporated by reference in their entirety. Examples of milbemycins also include milbemectin, milbemycin D and nemadectin.

Also included are the 5-oxo and 5-oxime derivatives of said avermectins and milbemycins, respectively.

The macrocyclic lactone compounds are known in the art and can easily be obtained commercially or through synthesis techniques known in the art. Reference is made to the widely available technical and commercial literature. For avermectins, such as ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", *J. Am. Chem. Soc.*, 103, 4216-4221. For doramectin, "Veterinary Parasitology", vol. 49, No. 1, Jul. 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

The avermectins and milbemycins demonstrate potent antiparasitic activity while being relatively non-toxic to most mammalian species. As a result, the avermectin/milbemycin family has been the focus of extensive chemical modification studies, which are outlined, for example, in U.S. Pat. Nos. 4,199,569; 4,285,963; 4,310,519; 4,423,209; 4,427,663; 4,457,920, 4,806,527; 4,831,016; 4,855,317; 4,859,657; 4,871,719; 4,873,224; 4,874,749; 4,895,837; 4,906,619, 4,920,148; 4,963,582; 4,973,711; 4,978,677; 5,015,630, 5,023,241, 5,030,622; 5,055,454; 5,055,596; 5,057,499; 5,077,308; 5,162,363; 5,169,839; 5,208,222; 5,244,879; 5,262,400; 5,637,703; 5,830,875; 7,250,402; and EP 0 212 867; 0 237 339; 0 241 146; 0 214 731; 0 194 125; and 0 170 006, all of which are hereby incorporated by reference in their entirety. Further modifications of members of the avermectin family are outlined, for example, in U.S. patent application Ser. Nos. 10/488,225; 10/498,858; 10/513,247; 10/539,274; 10/543,637; 10/543,638; 10/543,643, 10/544,274; 10/544, 281; 10/560,390; 10/568,715; 10/599,671; 11/317,932; 11/319,686; and 11/319,687, all of which are hereby incorporated by reference in their entirety. Chemical modifications have also been induced via spiking the fermentation broth with acids, which are subsequently incorporated at the C-25 position of the avermectins (EP 0 214 731, and *Arch. Biochem. Biophys* 1989, 269, 544-547). All of these documents and references cited therein, as well as the references cited herein, are expressly incorporated by reference.

Notwithstanding the excellent progress in antiparasitic research, concerns remain with respect to increasingly common reports of resistance among veterinary parasites (*Parasitology* 2005, 131, S179-190). Other concerns related to potential adverse effects on dung-dwelling insects essential for dung degradation have been raised with respect to endectocides. Thus, there remains an ongoing need for novel endectocides and anthelmintic treatments in veterinary medicine. It is an object of this invention to provide novel endectocides and anthelmintic compounds and formulations, as well as methods of treatment using such compounds. That the invention performs as herein described is surprising, unexpected and nonobvious.

While the macrocyclic lactones are well known antiparasitic compounds, there remains an ongoing need to combat the constantly evolving resistance of parasites. To this end, members of the paraherquamide family of spiroindoline derivatives have been found to also provide increased pesticidal activity to macrolactone-resistant strains of parasites in the larval stage (Gill, J. H., Lacey, E. *International J. Parasitology* 1998, 28, 863-877).

The paraherquamide family of compounds is known, see *Tet. Lett.* 1981, 22, 135, *J. Antibiotics* 1990, 43, 1380, and *J. Antibiotics* 1991, 44, 492; as well as the structurally related marcfortine family of compounds such as marcfortines A-C, see *J. Chem. Soc. —Chem. Comm.* 1980, 601 and *Tet. Lett.* 1981, 22, 1977. Further references to the paraherquamide derivatives can be found, for example, in WO 91/09961, WO 92/22555, WO 97/03988, WO 01/076370, WO 09/004,432, U.S. Pat. Nos. 5,703,078 and 5,750,695, all of which are hereby incorporated by reference in their entirety. Examples of marcfortine derivatives can be found, for example, in WO 92/22555, U.S. Pat. Nos. 4,866,060, 4,923,867, all of which are hereby incorporated by reference in their entirety. The syntheses of these and structurally similar compounds are also described therein.

The paraherquamides and marcfortines belong to the general class of spirodioxepinoindoles having the general structure exemplified in paraherquamide A:

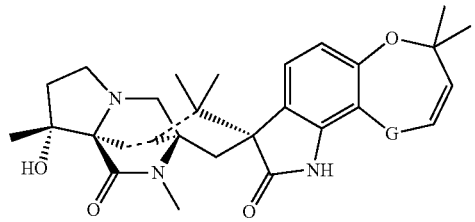

wherein G is an oxygen atom. Another representative member of this class is the 2-deoxy-paraherquamide also known as 2-desoxoparaherquamide. Marcfortines vary in that G may also be a bond or a methylene (CH₂) group, while the pyrrolidine ring is replaced with a piperidine ring.

The phenylpyrazoles as a class are known in the art and are described, for example in U.S. Pat. Nos. 5,885,607; 6,010,710; 6,083,519; 6,096,329; 6,395,765 and U.S. Pat. No. 6,867,229 (all assigned to Merial, Ltd.) as well as in U.S. Pat. Nos. 5,576,429; 5,122,530, U.S. patent application Ser. No. 11/825,050, and EP 295 177, the disclosures of which, as well as the references cited herein, are incorporated by reference.

This class of insecticides is known to possess excellent activity against insects such as ticks and fleas.

It will be appreciated that compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution.

The term "pharmaceutically acceptable salt or prodrug" is used throughout the specification to describe any pharmaceutically acceptable form (such as an ester, phosphate ester, salt of an ester or a related group) of a compound which, upon administration to a patient, provides the active compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

In cases where compounds are sufficiently basic or acidic to form stable non-toxic acid or base salts, the compounds may be in the form of a pharmaceutically acceptable salt. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, a-ketoglutarate, and a-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Another object of the present invention is to provide compounds with high activity and improved safety to the user and the environment, which are obtained by optimization of chemical, physical and biological properties such as solubility, melting point, stability, electronic and steric parameters, and the like.

For the purposes of this application, unless otherwise stated in the specification, the following terms have the definitions cited below:

(1) Alkyl refers to both straight and branched carbon chains; references to individual alkyl groups are specific for the straight chain (e.g. butyl=n-butyl). In one embodiment of alkyl, the number of carbons atoms is 1-20, in other embodiments of alkyl, the number of carbon atoms is 1-12, 1-10, 1-8 or 1-6 carbon atoms and in yet another embodiment of alkyl, the number of carbon atoms is 1-4 carbon atoms. Other ranges of carbon numbers are also contemplated depending on the location of the alkyl moiety on the molecule.

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by the term "alkyl", may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in another embodiment of alkenyl, the number of carbon atoms is 2-12, 2-10, 2-8 or 2-6 and in yet another embodiment of alkenyl, the number of carbon atoms is 2-4. Other ranges of carbon-carbon double bonds and carbon numbers are also contemplated depending on the location of the alkenyl moiety on the molecule.

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in another embodiment of alkynyl, the number of carbon atoms is 2-12, 2-10, 2-8 or 2-6. In yet another embodiment of alkynyl, the number of carbon atoms is 2-4. Other ranges of carbon-carbon double bonds and carbon numbers are also contemplated depending on the location of the alkenyl moiety on the molecule.

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{10}$ aromatic ring structure. Arylo refers to an aryl substituted at two adjacent sites. In some embodiments, the aryl ring may be fused to a non-aromatic ring, as long as the point of attachment to the core structure is through the aromatic ring. Aryl groups include, but are not limited to, phenyl, biphenyl, and naphthyl. In some embodiments aryl includes tetrahydronapthyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronapthyl, phenylcyclopropyl and indanyl; in another embodiment of aryl, the moiety is phenyl.

(5) Alkoxy refers to —O-alkyl, wherein alkyl is as defined in (1);

(6) Alkanoyl refers to formyl (—C(=O)H) and —C(=O)-alkyl, wherein alkyl is as defined in (1);

(7) Alkanoyloxy refers to —O—C(=O)-alkyl, wherein alkanoyl is as defined in (6);

(8) Alkanoylamino refers to —NH$_2$—C(=O)-alkyl, wherein alkanoyl is as defined in (6) and the amino (NH$_2$) moiety can be substituted by alkyl as defined in (1);

(9) Aminocarbonyl refers to —NH$_2$—C(=O), wherein the amino (NH$_2$) moiety can be substituted by alkyl as defined in (1);

(10) Alkoxycarbonyl refers to —C(=O)—O-alkyl, wherein alkoxy is as defined in (5);

(11) Alkenoyl refers to —C(=O)-alkenyl, wherein alkenyl is as defined in (2);

(12) Alkynoyl refers to —C(=O)-alkynyl, wherein alkynyl is as defined in (3);

(13) Aroyl refers to —C(=O)-aryl, wherein aryl is as defined above;

(14) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(15) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$));

(16) Heterocycle, heterocyclic or heterocyclo refer to fully saturated or unsaturated, including aromatic (i.e. "hetaryl") cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl]or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

In one embodiment, the compositions of the invention comprise an ivermectin or milbemycin derivative selected from moxidectin, milebemycin oxime, doramectin, abamectin, ivermectin, selamectin, and eprinomectin in combination with at least one spirodioxepinoindole derivative or a spirooxepinoindole derivative.

In one embodiment of the invention, the composition comprises ivermectin and paraherquamide.

In another embodiment of the invention, the composition comprises emamectin and paraherquamide.

In yet another embodiment of the invention, the composition comprises abamectin and paraherquamide.

In still another embodiment of the invention, the composition comprises moxidectin and paraherquamide.

In one embodiment of the invention, the composition comprises an avermectin or an avermectin derivative, a milbemycin or a milbemycin derivative and deoxyparaherquamide.

In another embodiment of the invention, the composition comprises an avermectin or avermectin derivative, milbemycin or a milbemycin derivative, a spirodioxepinoindole, and an arylpyrazole.

In another embodiment of the invention, the composition comprises an avermectin or avermectin derivative, mibemycin or a milbemycin derivative, a spirodioxepinoindole, and an arylpyrazole.

This invention further provides for a composition for the treatment or prophylaxis of parasite infestation in birds or mammals which may comprise:

(A) an effective amount of a spirodioxepinoindole derivative or a spirooxepinoindole derivative;
(B) a pharmaceutically effective amount of an ivermectin derivative of the formula (II):

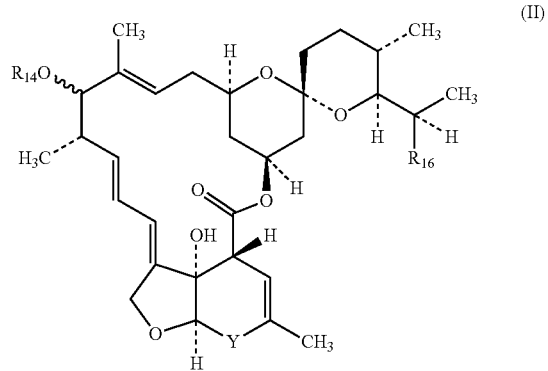

wherein:
$R_{14}$ represents —(CH$_2$)$_s$—O—Z
wherein,
s is 1 or 2;
Y represents —CH(OR$_{15}$)—, —C(=O)— or —C(=NOR$_{15}$);
$R_{15}$ represents hydrogen, alkyl or phenyl; and
$R_{16}$ represents —CH$_3$ or —CH$_2$CH$_3$;

Z is a mono- or disaccharide group, alkyl, alkenyl, alkynyl, acyl, alkylalkoxy, aryl, alkanoyloxy, alkoxycarbonyl, alkenoyl, alkynoyl, or aroyl; and
(C) a pharmaceutically acceptable carrier.

In another embodiment of the invention for the compound of formula (II), the composition for the treatment or prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (II):

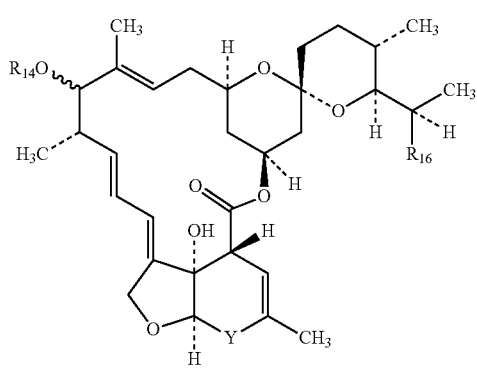
(II)

wherein:
$R_{14}$ represents —$(CH_2)_s$—O—Z
wherein,
s is 1 or 2;
Y represents —CH($OR_{15}$)—, —C(=O)— or —C(=$NOR_{15}$);
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_8$ alkyl, $C_1$-$C_8$ acyl, or $C_1$-$C_8$ alkylalkoxy; and
(C) a pharmaceutically acceptable carrier.

In another embodiment of the invention for the compound of formula (II), the composition for the treatment or prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (II):

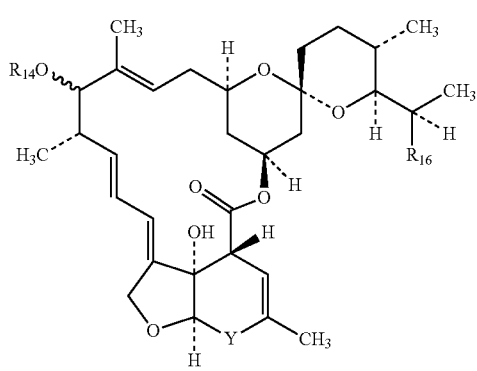
(II)

wherein:
$R_{14}$ represents —$(CH_2)_s$—O—Z
wherein,
s is 1;
Y represents —CH($OR_{15}$)—, —C(=O)— or —C(=$NOR_{15}$);
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_4$ alkyl, $C_1$-$C_4$ acyl, or $C_1$-$C_4$ alkylalkoxy; and
(C) a pharmaceutically acceptable carrier.

In an embodiment of the invention for formula (II), the composition for the treatment and prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (II):

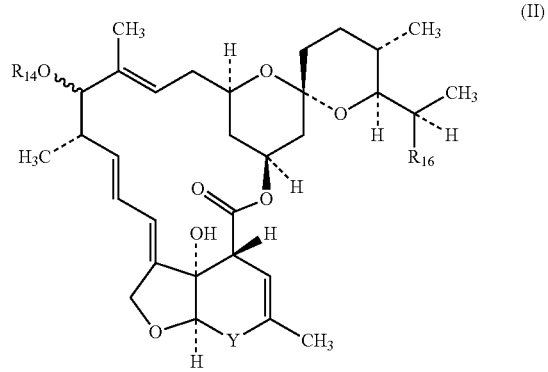
(II)

wherein:
$R_{14}$ represents —$(CH_2)_s$—O—Z
wherein,
s is 1;
Y represents —CH($OR_{15}$)—, —C(=O)— or —C(=$NOR_{15}$);
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_4$ alkyl, $C_1$-$C_4$ acyl, or $C_1$-$C_4$ alkylalkoxy; and
(C) a pharmaceutically acceptable carrier.

In another embodiment of the invention for formula (IIa), the composition for the treatment or prophylaxis of parasite infestation in birds or mammals may comprise:
(A) an effective amount of a spirodioxepinoindole derivative or a spirooxepinoindole derivative;

(B) a pharmaceutically effective amount of an ivermectin derivative of the formula (IIa):

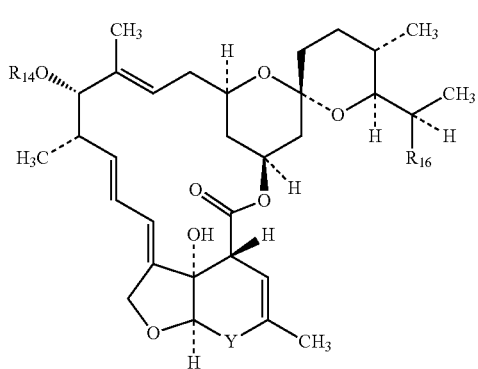

(IIa)

wherein:
$R_{14}$ represents —$(CH_2)_s$—O—Z
wherein,
s is 1 or 2;
Y represents —CH(OR$_{15}$)—, —C(=O)— or —C(=NOR$_{15}$);
$R_{15}$ represents hydrogen, $C_1$-$C_4$ alkyl or phenyl; and
$R_{16}$ represents —$CH_3$ or —$CH_2CH_3$;
Z is a mono- or disaccharide group, alkyl, alkenyl, alkynyl, acyl, alkylalkoxy, aryl, alkanoyloxy, alkoxycarbonyl, alkenoyl, alkynoyl, or aroyl; and
(C) a pharmaceutically acceptable carrier.

In another embodiment of the invention for the compound of formula (IIa), the composition for the treatment or prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (IIa):

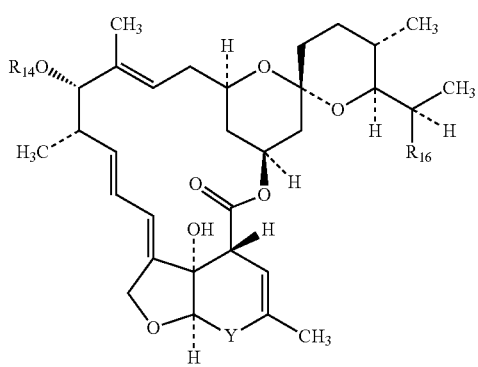

(IIa)

wherein:
$R_{14}$ represents —$(CH_2)_s$—O—Z
wherein,
s is 1 or 2;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_8$ alkyl, $C_1$-$C_8$ acyl, or $C_1$-$C_8$ alkylalkoxy; and
(C) a pharmaceutically acceptable carrier.

In another embodiment of the invention for the compound of formula (IIa), the composition for the treatment or prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (IIa):

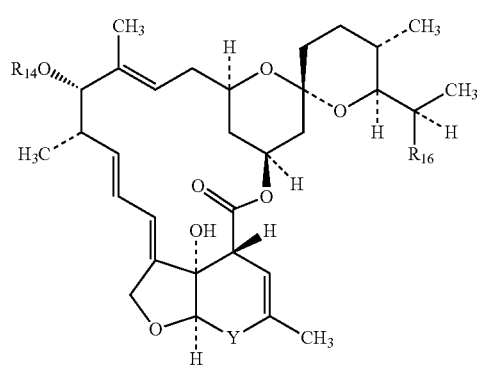

(IIa)

wherein:
$R_{14}$ represents —$(CH_2)_s$—O—Z
wherein,
s is 1;
Y represents —CH(OR$_{15}$)—, —C(=O)— or —C(=NOR$_{15}$);
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_4$ alkyl, $C_1$-$C_4$ acyl, or $C_1$-$C_4$ alkylalkoxy; and
(C) a pharmaceutically acceptable carrier.

In an embodiment of the invention for formula (IIa), the composition for the treatment and prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (IIa):

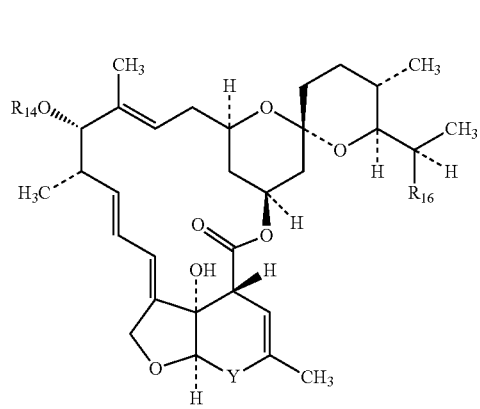

(IIa)

wherein:

$R_{14}$ represents —$(CH_2)_s$—O—Z wherein, s is 1;

Y represents —$CH(OR_{15})$—, —$C(=O)$— or —$C(=NOR_{15})$;

$R_{15}$ represents hydrogen, or $C_1$-$C_8$ alkyl; and $R_{16}$ represents —$CH_3$ or —$CH_2CH_3$;

Z is a mono- or disaccharide group, $C_1$-$C_4$ alkyl, $C_1$-$C_4$ acyl, or $C_1$-$C_4$ alkylalkoxy; and (C) a pharmaceutically acceptable carrier.

In an embodiment of the invention for formula (IIa), the composition for the treatment and prophylaxis of parasite infestation in birds or mammals may comprise:

(A) an effective amount of a spirodioxepinoindole derivative or a spirooxepinoindole derivative;

(B) a pharmaceutically effective amount of an ivermectin derivative of the formula (III):

(III)

wherein:

$R_{16}$ represents —$CH_3$ or —$CH_2CH_3$; and (C) a pharmaceutically acceptable carrier.

In another embodiment of the invention for formula (IIb), the composition for the treatment or prophylaxis of parasite infestation in birds or mammals may comprise:

(A) an effective amount of a spirodioxepinoindole derivative or a spirooxepinoindole derivative;

(B) a pharmaceutically effective amount of an ivermectin derivative of the formula (IIb):

(IIb)

wherein:

$R_{14}$ represents —$(CH_2)_s$—O—Z wherein, s is 1 or 2;

Y represents —$CH(OR_{15})$—, —$C(=O)$— or —$C(=NOR_{15})$;

$R_{15}$ represents hydrogen, or $C_1$-$C_8$ alkyl; and $R_{16}$ represents —$CH_3$ or —$CH_2CH_3$;

Z is a mono- or disaccharide group, $C_1$-$C_8$ alkyl, $C_1$-$C_8$ acyl, or $C_1$-$C_8$ alkylalkoxy; and (C) a pharmaceutically acceptable carrier.

In another embodiment of the invention for the compound of formula (IIb), the composition for the treatment or prophylaxis of parasite infestation in birds or mammals may comprise:

(A) an effective amount of a spirodioxepinoindole derivative or a spirooxepinoindole derivative;

Y represents —$CH(OR_{15})$—, —$C(=O)$— or —$C(=NOR_{15})$;

$R_{15}$ represents hydrogen, $C_1$-$C_4$ alkyl or phenyl; and $R_{16}$ represents —$CH_3$ or —$CH_2CH_3$;

Z is a mono- or disaccharide group, alkyl, alkenyl, alkynyl, acyl, alkylalkoxy, aryl, alkanoyloxy, alkoxycarbonyl, alkenoyl, alkynoyl, or aroyl; and (C) a pharmaceutically acceptable carrier.

In another embodiment of the invention for the compound of formula (IIb), the composition for the treatment or prophylaxis of parasite infestation in birds or mammals may comprise:

(A) an effective amount of a spirodioxepinoindole derivative or a spirooxepinoindole derivative;

(B) a pharmaceutically effective amount of an ivermectin derivative of the formula (IIb):

(IIb)

(B) a pharmaceutically effective amount of an ivermectin derivative of the formula (IIa):

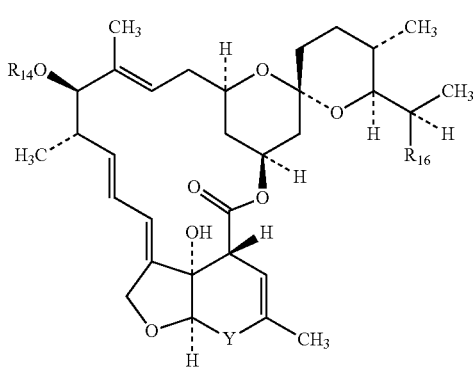
(IIa)

wherein:
$R_{14}$ represents —$(CH_2)_s$—O—Z
wherein,
s is 1;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_4$ alkyl, $C_1$-$C_4$ acyl, or $C_1$-$C_4$ alkylalkoxy; and
(C) a pharmaceutically acceptable carrier.

In an embodiment of the invention for formula (IIb), the composition for the treatment and prophylaxis of parasite infestation in birds or mammals may comprise:
(A) an effective amount of a spirodioxepinoindole derivative or a spirooxepinoindole derivative;
(B) a pharmaceutically effective amount of an ivermectin derivative of the formula (IIb):

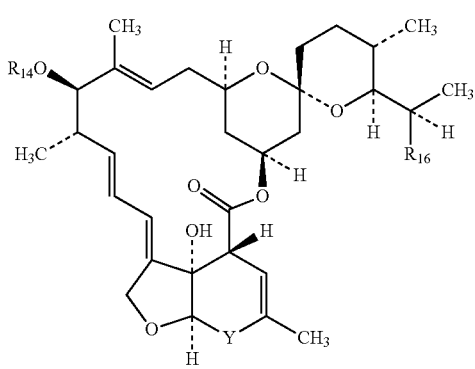
(IIb)

wherein:
$R_{14}$ represents —$(CH_2)_s$—O—Z
wherein,
s is 1;
Y represents —$CH(OR_{15})$—, —$C(=O)$— or —$C(=NOR_{15})$;
$R_{15}$ represents hydrogen, or $C_1$-$C_8$ alkyl; and
$R_{16}$ represents —$CH_3$ or —$CH_2CH_3$;
Z is a mono- or disaccharide group, $C_1$-$C_4$ alkyl, $C_1$-$C_4$ acyl, or $C_1$-$C_4$ alkylalkoxy; and
(C) a pharmaceutically acceptable carrier.

In an embodiment of the invention for formula (IIb), the composition for the treatment and prophylaxis of parasite infestation in birds or mammals may comprise:
(A) an effective amount of spirodioxepinoindole derivative or a spirooxepinoindole derivative;
(B) a pharmaceutically effective amount of an ivermectin derivative of the formula (IV):

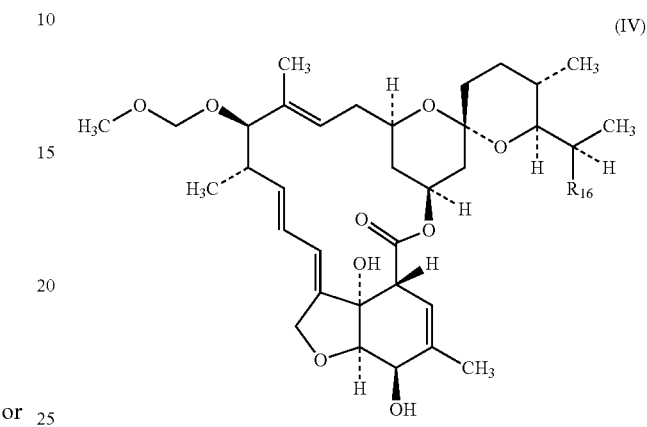
(IV)

wherein:
$R_{16}$ represents —$CH_3$ or —$CH_2CH_3$; and
(C) a pharmaceutically acceptable carrier.

In another embodiment of the invention, the composition may further comprise a spirodioxepinoindole derivative.

In yet another embodiment of the invention, the composition may comprise a macrocyclic lactone and a spirodioxepinoindole derivative.

Another aspect of the invention is the formation of parasiticidal compositions which may comprise the compounds of the invention. The composition of the invention may also be in a variety of forms which include, but are not limited to, oral formulations, injectable formulations, and topical, pour-on, dermal or subdermal formulations. The formulations are intended to be administered to an animal which includes but is not limited to mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds.

The composition of the invention may be in a form suitable for oral use, for example, as baits (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench formulations, dispersible powders or granules, premixes, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Formulations for oral use may be hard gelatin capsules, wherein the active ingredient is mixed with an inert solid diluent, for example, calcium carbonate, calcium phosphate or kaolin.

Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention may be in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range selected from the group consisting of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment of the glycol derivatives, the glycol may be selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion may include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants may include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition may be in paste form. Examples of embodiments in a paste form include but are not limited to those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the formulation, the formulation may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include, but is not limited to, a viscosity modifier selected from the group consisting of PEG 200, PEG 300, PEG 400, PEG 600, monoethanolamine, triethanolamine, glycerol, propylene glycol, polyoxyethylene (20) sorbitan mono-oleate (polysorbate 80 or Tween 80), and polyoxamers (e.g., Pluronic L 81); an absorbent selected from the group consisting of magnesium carbonate, calcium carbonate, starch, and cellulose and its derivatives; and a colorant selected from the group consisting of titanium dioxide iron oxide, and FD&C Blue #1 Aluminum Lake.

The compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations may include, by way of non-limiting example, emulsions, creams, ointments, gels, pastes, powders, shampoos, pour-on formulations, ready-to-use formulations, spot-on solutions and suspensions, dips and sprays. Topical application of an inventive compound or of a composition including at least one inventive compound among active agent(s) therein, a spot-on, spray-on or pour-on composition, may allow for the inventive composition to be absorbed through the skin to achieve systemic levels, distributed through the sebaceous glands or on the surface of the skin achieving levels throughout the haircoat. When the compound is distributed through the sebaceous glands, they may act as a reservoir, whereby there may be a long-lasting effect (up to several months) effect. Spot-on formulations are typically applied in a localized region which refers to an area other than the entire animal. In one embodiment of a localized region, the location may be between the shoulders. In another embodiment of a localized region it may be a stripe, e.g. a stripe from head to tail of the animal.

Pour-on formulations are described in U.S. Pat. No. 6,010, 710, also incorporated herein by reference. The pour-on formulations may be advantageously oily, and generally comprise a diluent or vehicle and also a solvent (e.g. an organic solvent) for the active ingredient if the latter is not soluble in the diluent.

Organic solvents that may be used in the invention include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, coconut oils etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil), (c) cationic surfactants such as water-soluble quaternary ammonium salts of formula $N^+R'R''R'''R''''$, $Y^-$ in which the radicals R are optionally hydroxylated hydrocarbon radicals and $Y^-$ is an anion of a strong acid such as the halide, sulphate and sulphonate anions; cetyltrimethylammonium bromide is among the cationic surfactants which can be used, (d) amine salts of formula $N^+HR'R''R'''$ in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

The solvent will be used in proportion with the concentration of the compounds of the invention and their solubilities in this solvent. It will be sought to have the lowest possible volume. The vehicle makes up the difference to 100%.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in ready-to-use solution form as is described in U.S. Pat. No. 6,395,765, incorporated herein by reference. In addition to the compounds of the invention, the ready-to-use solution may contain a crystallization inhibitor, an organic solvent and an organic co-solvent.

In one embodiment of the amount of crystallization inhibitor, the crystallization inhibitor may be present in a proportion of about 1 to about 30% (w/v) or about 5 to about 15%. In other embodiments, the amount of crystallization inhibitor in the inventive formulations may be about 1% to about 20%, about 1% to about 15%, or about 1% to about 10% (w/w).

In some embodiments, the organic solvent may have a dielectric constant of between about 10 and 35 or between about 20 and 30, the content of this organic solvent in the overall composition representing the complement to 100% of the composition.

In some embodiments, the organic co-solvent may have a boiling point of below about 100° C., or below about 80° C. In other embodiments, the organic co-solvent may have a boiling point of below about 250° C., below about 230° C., below about 210° C. or below about 200° C. In other embodiments, the organic co-solvent may have a dielectric constant of between about 10 and 40 or between about 20 and 30. In some embodiments, the co-solvent may be present in the composition in a organic co-solvent/organic solvent weight/weight (W/W) ratio of between about 1/15 and 1/2. The solvent may act as to improve solubility or as a drying promoter, and is miscible with water and/or with the organic solvent.

The formulation may also comprise an antioxidizing agent intended to inhibit oxidation in air, this agent being present in a proportion selected from a range consisting of about 0.005 to about 1% (w/v) and about 0.01 to about 0.05%.

The type of crystallization inhibitor used in the inventive formulations is not limited as long as it functions to inhibit crystallization or precipitation of the active or inactive agents from the formulation. Crystallization inhibitors which are useful for the invention may include but are not limited to:

(a) polyvinylpyrrolidone, polyvinyl alcohols, copolymers of vinyl acetate and of vinylpyrrolidone, polyethylene glycols, benzyl alcohol, N-methylpyrrolidone, mannitol, glycerol, sorbitol or polyoxyethylenated esters of sorbitan; lecithin or sodium carboxymethylcellulose; or acrylic derivatives, such as methacrylates and others;

(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and Y is an anion of a strong acid, such as halide, sulphate and sulphonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the skin or fur; that is to say without a tendency towards sticking or towards a sticky appearance, despite the high concentration of active material.

In one embodiment of the antioxidizing agents, the agents are those conventional in the art and include but are not limited to butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied may be of the order of about 0.3 to about 1 ml. In one embodiment for the volume, the volume may be on the order of about 0.5 ml, for cats and on the order of about 0.3 to about 3 ml for dogs, depending on the weight of the animal.

In another embodiment of the invention, application of a spot-on formulation according to the present invention may also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

For spot-on formulations, the carrier may be a liquid carrier vehicle as described in U.S. Pat. No. 6,426,333 (incorporated herein by reference), which in one embodiment of the spot-on formulation may comprise a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol.

The liquid carrier vehicle may optionally contain a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Spot-on formulations may be prepared by dissolving the active ingredients into the pharmaceutically or veterinary acceptable vehicle. Alternatively, the spot-on formulation may be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Dosage forms may contain from about 0.5 mg to about 5 g of an active agent. In one embodiment of the dosage form, the dosage is from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the formulation at a concentration of about 0.05 to 10% weight/volume. In another embodiment of the invention, the active agent may be present in the formulation as a concentration from about 0.1 to 2% weight/volume. In yet another embodiment of the invention, the active agent may be present in the formulation as a concentration from about 0.25 to about 1.5% weight/volume. In still another embodiment of the invention, the active agent may be present in the formulation as a concentration about 1% weight/volume.

In another embodiment of the invention, the active composition may be administered via a drench, and may be administered either topically or orally. Drench formulations are those in which the liquid containing the compositions of the invention is administered to the mouth or throat of the animal, or poured onto the skin or coat of the animal.

The invention is also directed toward a method of treating an animal (e.g. a mammal or bird) against ectoparasitic infection by administering an ectoparasiticidally effective amount of the composition of the invention. Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

In one embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes*, and *Felicola*.

In another embodiment for treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like). In yet another embodiment for the treatment against ectoparasites, the ectoparasite is a flea and/or tick. Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabici* and *Psoroptes ovis*. The above list is not exhaustive and other ectoparasites are well known in the art to be harmful to animals and humans. These include, for example migrating dipterous larvae.

The compositions of the invention can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris*, and *Trichostrongylus*.

In another embodiment of the invention, the compounds and compositions of the invention are suitable for controlling pests such as insects selected from the group consisting of *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:
(1) from the order of Isopoda, for example *Oniscus asellus, Armadillidium vulgare* and *Porcellio scaber;*
(2) from the order of Diplopoda, for example *Blaniulus guttulatus;*
(3) from the order of Chilopoda, for example *Geophilus carpophagus* and *Scutigera* spp.;
(4) from the order of Symphyla, for example *Scutigerella immaculata;*
(5) from the order of Thysanura, for example *Lepisma saccharina;*
(6) from the order of Collembola, for example *Onychiurus armatus;*
(7) from the order of Blattaria, for example *Blatta orientalis, Periplaneta americana, Leucophaea maderae* and *Blattella germanica;*
(8) from the order of Hymenoptera, for example *Diprion* spp., *Hoplocampa* spp., *Lasius* spp., *Monomorium pharaonis* and *Vespa* spp.;
(9) from the order of Siphonaptera, for example *Xenopsylla cheopis* and *Ceratophyllus* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici;*

(12) from the class of Bivalva, for example, *Dreissena* spp.;

(13) from the order of Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.;

(15) from the class of Gastropoda, for example, *Arion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Acylostoma braziliensis, Ancylostoma* spp., *Ascaris lubnicoides, Ascaris* spp., *Brugia malayi, Brugia timoni, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti;*

(17) from the order of Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma pini, Aphis* spp., *Arboridia apicalis, Aspidiella* spp., *Aspidiotus* spp., *Atanus* spp., *Aulaconthum solani, Bemisia* spp., *Brachycaudus helichrysii, Brachycolus* spp., *Brevicoryne brassicae, Calli gypona manginata, Carneocephala fulgida, Cenatovacuna lanigena, Cencopidae, Cenoplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphonina* spp., *Diaspis* spp., *Dorsalis* spp., *Drosicha* spp., *Dysaphis* spp., *Dysmicoccus* spp., *Empoasca* spp., *Eniosoma* spp., *Enythnoneuna* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii;*

(19) from the order of Isoptera, for example, *Reticulitermes* spp., *Odontotermes* spp.;

(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofinannophila pseudospretella, Homona magnanima, Hyponomeuta padella, Laphygma* spp., *Lithocolletis blancardella, Lithophane antennata, Loxagrotis albicosta,*

Lymantria spp., Malacosoma neustria, Mamestra brassicae, Mocis repanda, Mythimna separata, Oria spp., Oulema oryzae, Panolis flammea, Pectinophora gossypiella, Phyllocnistis citrella, Pieris spp., Plutella xylostella, Prodenia spp., Pseudaletia spp., Pseudoplusia includens, Pyrausta nubilalis, Spodoptera spp., Thermesia gemmatalis, Tinea pellionella, Tineola bisselliella, Tortrix viridana, Trichoplusia spp.;

(21) from the order of Orthoptera, for example, Acheta domesticus, Blatta orientalis, Blattella germanica, Gryllotalpa spp., Leucophaea maderae, Locusta spp., Melanoplus spp., Periplaneta americana, Schistocerca gregaria;

(22) from the order of Thysanoptera, for example, Baliothrips biformis, Enneothrips flavens, Frankliniella spp., Heliothrips spp., Hercinothrips femoralis, Kakothrips spp., Rhipiphorothrips cruentatus, Scirtothrips spp., Taeniothrips cardamoni, Thrips spp.;

(23) from the class of Protozoa, for example, Eimeria spp.

In each aspect of the invention, the compounds and compositions of the invention can be applied against a single pest or combinations thereof.

In some embodiments, the compositions of the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

In other embodiments, the compositions of the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development.

The compounds of the invention or their salts may be employed as such or in the form of their preparations (formulations) as combinations with other pesticidally active substances, such as, for example, insecticides, attractants, sterilants, acaricides, nematicides, herbicides, fungicides, and with safeners, fertilizers and/or growth regulators, for example as a premix/readymix.

The insecticides may include, for example, phosphoric esters, carbamates, carboxylic esters, chlorinated hydrocarbons, phenylureas, substances prepared by microorganisms.

Examples of insecticides which may optionally be admixed include but are not limited to: phosphoric esters, such as azinphos-ethyl, azinphos-methyl, α-1(4-chlorophenyl)-4-(O-ethyl, S-propyl)phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, poxim, pirimiphos-ethyl, pirimiphos-methyl, profenofos, prothiofos, sulfprofos, triazophos and trichlorphon; carbamates, such as aldicarb, bendiocarb, α-2-(1-methylpropyl)-phenyl methylcarbamate, butocarboxim, butoxycarboxim, carbaryl, carbofuran, carbosulfan, cloethocarb, isoprocarb, methomyl, oxamyl, pirimicarb, promecarb, propoxur and thiodicarb; organosilicon compounds (e.g. dimethyl(phenyl)silyl-methyl 3-phenoxybenzyl ethers, such as dimethyl-(4-ethoxyphenyl)-silylmethyl 3-phenoxybenzyl ether) or (dimethylphenyl)-silyl-methyl 2-phenoxy-6-pyridylmethyl ethers such as, for example, dimethyl-(9-ethoxyphenyl)-silylmethyl 2-phenoxy-6-pyridylmethyl ether or [(phenyl)-3-(3-phenoxyphenyl)-propyl[(dimethyl)-silanes such as, for example, (4-ethoxyphen-yl)-[3-(4-fluoro-3-phenoxyphenyl-propyl]dimethyl-silane, silafluofen; pyrethroids (which are also useful for their repellent properties, e.g. against mosquitoes), such as allethrin, alphamethrin, bioresmethrin, byfenthrin, cycloprothrin, cyfluthirin, decamethrin, cyhalothrin, cypermethrin, deltamethrin, alpha-cyano-3-phenyl-2-methylbenzyl 2,2-dimethyl-3-(2-chloro-2-trifluoromethylvinyl)cyclopropane-carboxylate, fenpropathrin, fenfluthrin, fenvalerate, flucythrinate, flumethrin, fluvalinate, permethrin, resmethrin and tralomethrin; nitroimines and nitromethylenes, such as 1-[(6-chloro-3-pyridinyl)-methyl]-4,5-dihydro-N-nitro-1H-imidazole-2-amine (imidacloprid), N-[(6-chloro-3-pyridyl)-methyl]-N$^2$-cyano-N$^1$-methylacetamide (NI-25); abamectin, AC 303, 630 (chlorfenapyr), acephate, acrinathrin, alanycarb, aldoxycarb, aldrin, amitraz, azamethiphos, Bacillus thuringiensis, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, 0-2-tert-butyl-pyrimidin-5-yl-o-isopropylphosphorothiate, thiocyclam, thiofanox, thiometon, tralomethrin, triflumuron, trimethacarb, vamidothion, Verticillium Lacanii, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alphacypermethrin, cyophenothrin, cyromazine, dazomet, DDT, demeton-5-methylsulphone, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, formothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous chloride, metam, metarthizium, anisopliae, methacrifos, methamidophos, methidathion, methiocarb, methoprene, methoxychlor, methyl isothiocyanate, metolcarb, mevinphos, monocrotophos, naled, Neodiprion sertifer NPV, nicotine, omethoate, oxydemeton-methyl, pentachlorophenol, petroleum oils, phenothrin, phenthoate, phorate.

Other insecticides that may optionally be admixed may also be from the class of the compounds described by U.S. Pat. No. 7,001,903, which is hereby incorporated by reference in its entirety.

Fungicides which may optionally be admixed are include but are not limited to:

(1) Triazoles which include but are not limited to: azaconazole, propiconazole, tebuconazole, cyproconazole, metconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

(2) Imidazoles which include but are not limited to: imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

(3) "Methyl(E)-2-phenyl-3-methoxyacrylate" compounds which include but are not limited to:

methyl (E)-2-[2-[6-(2-cyanophenoxy)pyrimidin-4-yloxy]phenyl]3-methoxyacrylate,
methyl (E)-2-[2-[6-(2-thioamidophenoxy)pyrimidin-4-yloxy]phenyl]-3-methoxyacrylate,
methyl (E)-2-[2-[6-(2-fluorophenoxy)pyrimidin-4-yloxy]phenyl]-3-methoxyacrylate,
methyl (E)-2-[2-[6-(2,6-difluorophenoxy)pyrimidin-4-yloxy]phenyl]-3-methoxyacrylate,
methyl (E)-2-[2-[3-(pyrimidin-2-yloxy)phenoxy]phenyl]-3-methoxyacrylate,
methyl (E)-2-[2-[3-(5-methylpyrimidin-2-yloxy)-phenoxy]phenyl]-3-methoxyacrylate,
methyl (E)-2-[2-[3-(phenyl-sulphonyloxy)phenoxy]phenyl-3-methoxyacrylate,
methyl (E)-2-[2-[3-(4-nitrophenoxy)phenoxy]phenyl]-3-methoxyacrylate,
methyl (E)-2[2-phenoxyphenyl]-3-methoxyacrylate,
methyl (E)-2-[2-(3,5-dimethyl-benzoyl)pyrrol-1-yl]-3-methoxyacrylate,
methyl (E)-2-[2-(3-methoxyphenoxy)phenyl]-3-methoxyacrylate,
methyl (E)-2[2-(2-phenylethen-1-yl)-phenyl]-3-methoxyacrylate,
methyl (E)-2-[2-(3,5-dichlorophenoxy)pyridin-3-yl]-3-methoxyacrylate,
methyl (E)-2-(2-(3-(1,1,2,2-tetrafluoroethoxy)phenoxy)phenyl)-3-methoxyacrylate,
methyl (E)-2-(2-[3-(alpha-hydroxybenzyl)phenoxy]phenyl)-3-methoxyacrylate,
methyl (E)-2-(2-(4-phenoxypyridin-2-yloxy)phenyl)-3-methoxyacrylate,
methyl (E)-2-[2-(3-n-propyloxyphenoxy)phenyl]3-methoxyacrylate,
methyl (E)-2-[2-(3-isopropyloxyphenoxy)phenyl]-3-methoxyacrylate,
methyl (E)-2-[2-[3-(2-fluorophenoxy)phenoxy]phenyl]-3-methoxyacrylate,
methyl (E)-2-[2-(3-ethoxyphenoxy)phenyl]-3-methoxyacrylate,
methyl (E)-2-[2-(4-tert-butyl-pyridin-2-yloxy)phenyl]-3-methoxyacrylate,
methyl (E)-2-[2-[3-(3-cyanophenoxy)phenoxy]phenyl]-3-methoxyacrylate,
methyl (E)-2-[2-[(3-methylpyridin-2-yloxymethyl)phenyl]-3-methoxyacrylate,
methyl (E)-2-[2-[6-(2-methylphenoxy)pyrimidin-4-yloxy]phenyl]-3-methoxyacrylate,
methyl (E)-2-[2-(5-bromo-pyridin-2-yloxymethyl)phenyl]-3-methoxyacrylate,
methyl (E)-2-[2-(3-(3-iodopyridin-2-yloxy)phenoxy)phenyl]-3-methoxyacrylate,
methyl (E)-2-[2-[6-(2-chloropyridin-3-yloxy)pyrimidin-4-yloxy]phenyl]-3-methoxyacrylate,
methyl (E),(E)-2-[2-(5,6-di-methylpyrazin-2-ylmethyloxyiminomethyl)phenyl]-3-methoxyacrylate,
methyl (E)-2-{2-[6-(6-methylpyridin-2-yloxy)pyrimidin-4-yloxy]phenyl}-3-methoxyacrylate,
methyl (E),(E)-2-{2-(3-methoxyphenyl)methyloximinomethyl]-phenyl}-3-methoxyacrylate,
methyl (E)-2-{2-(6-(2-azidophenoxy)-pyrimidin-4-yloxy]phenyl}-3-methoxyacrylate,
methyl (E),(E)-2-{2-[6-phenylpyrimidin-4-yl)-methyloximinomethyl]phenyl}-3-methoxyacrylate,
methyl (E),(E)-2-{2-[(4-chlorophenyl)-methyloximinomethyl]-phenyl}-3-methoxyacrylate,
methyl (E)-2-{2-[6-(2-n-propylphenoxy)-1,3,5-triazin-4-yloxy]phenyl}-3-methoxyacrylate, and
methyl (E),(E)-2-{2-[(3-nitrophenyl)methyloximinomethyl]phenyl}-3-methoxyacrylate;

(4) Succinate Dehydrogenase Inhibitors which include but are not limited to:

(a) fenfuram, furcarbanil, cyclafluramid, furmecyclox, seedvax, metsulfovax, pyrocarbolid, oxycarboxin, shirlan, mebenil (mepronil), benodanil, flutolanil (Moncut);

(b) naphthalene derivatives such as terbinafine, naftifine, butenafine, 3-chloro-7-(2-aza-2,7,7-trimethyl-oct-3-en-5-ine);

(c) sulphenamides such as dichlofluanid, tolylfluanid, folpet, fluorfolpet; captan, captofol;

(d) benzimidazoles such as carbendazim, benomyl, furathiocarb, fuberidazole, thiophonatmethyl, thiabendazole or their salts;

(e) morpholine derivatives such as fenpropimorph, falimorph, dimethomorph, dodemorph, aldimorph, fenpropidine and their arylsulphonates, such as, for example, p-toluenesulphonic acid and p-dodecylphenyl-sulphonic acid;

(f) dithiocarbamates, cufraneb, ferbam, mancopper, mancozeb, maneb, metam, metiram, thiram zeneb, ziram;

(g) benzothiazoles, such as 2-mercaptobenzothiazole;

(h) benzamides, such as 2,6-dichloro-N-(4-trifluoromethylbenzyl)-benzamide;

(i) boron compounds, such as boric acid, boric esters, borax;

(j) formaldehyde and formaldehyde-releasing compounds, such as benzyl alcohol mono-(poly)-hemiformal, oxazolidine, hexa-hydro-5-triazines, N-methylolchloroacetamide, paraformaldehyde, nitropyrin, oxolinic acid, tecloftalam;

(k) tris-N-(cyclohexyldiazeniumdioxy)-aluminium, N-(cyclo-hexyldiazeniumdioxy)-tri-butyltin or K salts, bis-N-(cyclohexyldiazeniumdioxy)-copper, N-methylisothiazolin-3-one, 5-chloro-N-methylisothiazolin-3-one, 4,5-dichloro-N-octylisothiazolin-3-one, N-octyl-isothiazolin-3-one, 4,5-trimethylene-isothiazolinone, 4,5-benzoisothiazolinone, N-methylolchloroacetamide;

(l) aldehydes, such as cinnamaldehyde, formaldehyde, glutaraldehyde, β-bromo-cinnamaldehyde;

(m) thiocyanates, such as thiocyanatomethylthiobenzothiazole, methylenebisthiocyanate, and the like;

(n) quaternary ammonium compounds, such as benzyldimethyltetradecylammonium chloride, benzyldimethyldodecylanmuonium chloride, didecyldimethylammonium chloride;

(o) iodine derivatives, such as diiodomethyl p-tolyl sulphone, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;

(p) phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;

(q) microbicides having an activated halogen group, such as chloroacetamide, bronopol, bronidox, tectamer, such as 2-bromo-2-nitro-1,3-propanediol, 2-bromo-4'-hydroxyacetophenone, 2,2-dibromo-3-nitrile-propionamide, 1,2-dibromo-2,4-dicyanobutane, β-bromo-β-nitrostyrene;

(r) pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;

(s) metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;

(t) metal salts, such as copper hydroxycarbonate, sodium dichromate, potassium dichromate, potassium chromate, copper sulphate, copper chloride, copper borate, zinc fluorosilicate, copper fluorosilicate, and mixtures with fixatives;

(u) oxides, such as tributyltin oxide, $Cu_2O$, CuO, ZnO;

(v) dialkyldithiocarbamates, such as Na and Zn salts of dialkyldithiocarbamates, tetramethylthiuram disulphide, potassium N-methyl-dithiocarbamate;

(w) nitriles, such as 2,4,5,6-tetrachloroisophthalodinitrile, disodium cyano-dithioimido-carbamate;

(x) quinolines, such as 8-hydroxyquinoline, and their Cu salts;

(y) mucochloric acid, 5-hydroxy-2(5H)-furanone;

(z) 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxymethyl-N'-methyl-dithiocarbamate, 2-oxo-2-(4-hydroxy-phenyl)acetohydroximic acid chloride, phenyl-(2-chloro-cyano-vinyl)sulphone, phenyl-(1,2-dichloro-2-cyano-vinyl)sulphone; and (aa) Ag-, Zn- or Cu-containing zeolites, alone or enclosed in polymeric active compounds, or (bb) mixtures of more than one of the abovementioned fungicides.

Herbicides which are known from the literature and which may be combined with the inventive compositions are, for example, the following active substances (Note: the compounds are either designated by the common name according to the International Organization for Standardization (ISO) or using the chemical name, if appropriate together with a customary code number):

acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; amitrol; AMS, i.e. ammonium sulfamate; anilofos; asulam; atrazine; azafenidin; azimsulfuron (DPX-A8947); aziprotryn; barban; BAS 516 H, i.e. 5-fluoro-2-phenyl-4H-3,1-benzoxazin-4-one; beflubutamid; benazolin(-ethyl); benfluralin; benfuresate; bensulfuron (-methyl); bensulide; bentazone(-sodium); benzobicyclone; benzofenap; benzofluor; benzoylprop(-ethyl); benzthiazuron; bialaphos (bilanafos); bifenox; bispyribac(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon(-methyl or -ethyl), cinmethylin; cinosulfuron; clethodim; clefoxydim, clodinafop and its ester derivatives (for example clodinafop-propargyl); clomazone; clomeprop; cloproxydim; clopyralid; clopyrasulfuron (-methyl); cloransulam(-methyl); cumyluron (JC 940); cyanazine; cycloate; cyclosulfamuron (AC 104); cycloxydim; cycluron; cyhalofop and its ester derivatives (for example butyl-ester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid(-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl] ethanesulfonamide; fenoprop; fenoxan, fenoxapropand fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); fluchloralin; flufenacet (FOE 5043), flufenpyr, flumetsulam; flumeturon; flumiclorac (-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; fluorochloridone; fluoroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate(-ammonium); glyphosate(-isopropylammonium); halosafen; halosulfuron (-methyl) and its esters (for example the methyl ester, NC-319); haloxyfop and its esters; haloxyfop-P(=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr, imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil, linuron; MCPA; MCPB; mecoprop; mefenacet; mefluidid; mesosulfuron(-methyl); mesotrione; metam, metamifop, metamitron; metazachlor; methabenzthiazuron; methazole; methoxyphenone; methyldymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methyl-pentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenop-butyl; pretilachlor; primisulfuron(-methyl); procarbazone(-sodium); procyazine; prodiamine; profluazole, profluralin; proglinazine(-ethyl); prometon; prometryn; propachlor; propanil; propaquizafop; propazine; propham; propisochlor; propoxycarbazone(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron(-ethyl); pyrazoxyfen; pyribenzoxim; pyributicarb; pyridafol; pyridate; pyriftalid, pyrimidobac(-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluoron; thiazopyr (Mon-13200); thidiazimin (SN-24085); thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(-sodium), trifluralin; triflusulfuron and esters (e.g. methyl ester, DPX-66037); trimeturon; tritosulfuron; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127; KIH-2023 and KIH5996.

Appropriate herbicide safeners may include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Components which may be employed for the active substances according to the invention in mixed formulations, for example, known active compounds which are based on an inhibition of, for example, acetolactate synthase, acetyl-coenzyme A carboxylase, PS I, PS II, HPPDO, phytoene desaturase, protoporphyrinogen oxidase, glutamine synthetase, cellulose biosynthesis, 5-enolpyruvylshikimate-3-phosphate synthetase. Such compounds, and also other compounds which may be employed, whose mechanism of action is to a degree unknown or different, are described, for example, in Weed Research 26, 441-445 (1986), or "The Pesticide Manual", 12th Edition 2000 (hereinbelow also abbreviated to "PM"), The British Crop Protection Council and the Royal Soc. of Chemistry (editors) and literature cited therein.

The compositions of the invention may be formulated in various ways, depending on the prevailing biological and/or chemico-physical parameters. Examples of possible formulations which may be suitable include, but are not limited to: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

Solid state forms of the compositions may also be prepared by methods known in the art, e.g. Byrn et al., "Solid-State Chemistry of Drugs", $2^{nd}$ Edition, SSCI Inc., (1999); Glusker et al., "Crystal Structure Analysis—A Primer", $2^{nd}$ Edition, Oxford University Press, (1985).

The formulations mentioned may be prepared in a manner known per se, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "Chemische Technologie" [Chemical Technology], Volume 7, C. Hauser Verlag, Munich, 4th Edition 1986; Wade van Valkenburg, "Pesticide Formulations", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N. J.; H. v. Olphen, "Introduction to Clay Colloid Chemistry", 2nd Ed., J. Wiley & Sons, N.Y.; C. Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag, Munich, 4th Ed. 1986.

Wettable powders are preparations which are uniformly dispersible in water and which, besides the compounds of the invention, also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the compounds of the invention are, for example, ground finely in conventional apparatuses such as hammer mills, blower mills and air-jet mills and mixed with the formulation auxiliaries, either concomitantly or thereafter. Emulsifiable concentrates are prepared, for example, by dissolving the compounds of the invention in an organic solvent, for example butanol, cyclohexanone, dimethylformamide, xylene or else higher-boiling aromatics or hydrocarbons or mixtures of these, with addition of one or more ionic and/or nonionic surfactants (emulsifiers). Emulsifiers which may be used are, for example: calcium salts of alkylarylsulfonic acids, such as calcium dodecylbenzenesulfonate or nonionic emulsifiers, such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters or polyoxyethylene sorbitan esters such as polyoxyethylene sorbitan fatty acid esters.

Dusts may be obtained by grinding the active substance with finely divided solid substances, for example talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above for example in the case of the other formulation types.

Emulsions, for example oil-in-water emulsions (EW), may be prepared for example by means of stirrers, colloid mills and/or static mixtures using aqueous organic solvents and, if appropriate, surfactants as they have already been mentioned above for example in the case of the other formulation types.

Granules may be prepared either by spraying the compounds of the invention onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances may also be granulated in the manner which is conventional for the production of fertilizer granules, if desired in a mixture with fertilizers.

Water-dispersible granules may be prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, p. 8-57. In general, the agrochemical preparations may comprise a range selected from the group consisting of about 0.1 to about 99% by weight and about 0.1 to about 95% by weight, of compounds of the invention.

The concentration of compounds of the invention in wettable powders may be, for example, about 10 to about 90% by weight, the remainder to 100% by weight being composed of customary formulation components. In the case of emulsifiable concentrates, the concentration of compounds of the invention may amount to ranges selected from the group consisting of about 1% to about 90% and about 5% to about 80% by weight. Formulations in the form of dusts may usually comprise in the range selected from the group consisting of about 1% to about 30% by weight of compounds of the invention and about 5% to about 20% by weight of compounds of the invention. For sprayable solutions, formulations may comprise a range selected from the group consisting of about 0.05% to about 80% by weight of compounds of the invention and about 2% to about 50% by weight of compounds of the invention. In the case of water-dispersible granules, the content of compounds of the invention may depend partly on whether the compounds of the invention are in liquid or solid form and on which granulation auxiliaries, fillers and the like are being used. The water-dispersible granules, for example, may comprise a range selected from the group consisting of between about 1 and about 95% and between about 10% and about 80% by weight.

In addition, the formulations of compounds of the invention mentioned may comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The mixtures according to the invention may be applied via the soil either pre-emergently or post-emergently. The mixtures according to the invention may also be applied via the leaf. The mixtures according to the invention may be employed for seed dressing. It may further be possible to apply the mixtures according to the invention via an irrigation system, for example via the water for irrigation.

Additional pharmaceutical, pesticidal or veterinarily active ingredients, which include, but are not limited to, parasiticidals including acaricides, anthelmintics, endectocides and insecticides, may also be added to the compositions of the invention. Anti-parasitic agents may include both ectoparasiticisal and endoparasiticidal agents. Veterinary pharmaceutical agents are well-known in the art (see e.g. Plumb' *Veterinary Drug Handbook*, $5^{th}$ Edition, ed. Donald C. Plumb, Blackwell Publishing, (2005) or *The Merck Veterinary Manual*, $9^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil HCl, allopurinol, alprazolam, altrenogest, amantadine HCl, amikacin sulfate, aminocaproic acid, aminopentamide hydrogen sulfate, aminophylline/theophylline, amiodarone HCl, amitraz, amitriptyline HCl, amlodipine besylate, ammonium chloride, ammonium molybdenate, amoxicillin, amoxicillin, clavulanate potassium, amphotericin B desoxycholate, amphotericin B lipid-based, ampicillin, amprolium HCl, antacids (oral), antivenin, apomorphione HCl, apramycin sulfate, ascorbic acid, asparaginase, aspiring, atenolol, atipamezole HCl, atracurium besylate, atropine sulfate, aurnofin, aurothioglucose, azaperone, azathioprine, azithromycin, baclofen, barbituates, benazepril HCl, betamethasone, bethanechol chloride, bisacodyl, bismuth subsalicylate, bleomycin sulfate, boldenone undecylenate, bromides, bromocriptine mesylate, budenoside, buprenorphine HCl, buspirone HCl, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur HCl, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine HCl, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol HCl, clindamycin, clofazimine, clomipramine HCl, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine HCl, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine HCl, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin HCl, digoxin, dihydrotachysterol (DHT), diltiazem HCl, dimenhydrinate, dimercaprol/BAL, dimethyl sulfoxide, dinoprost tromethamine, diphenylhydramine HCl, disopyramide phosphate, dobutamine HCl, docusate/DSS, dolasetron mesylate, domperidone, dopamine HCl, doramectin, doxapram HCl, doxepin HCl, doxorubicin HCl, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol HCl, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine HCl, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline HCl, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol HCl, isotretinoin, isoxsuprine HCl, itraconazole, ivermectin, kaolin/pectin, ketamine HCl, ketoconazole, ketoprofen, ketorolac tromethamine, lactulose, leuprolide, levamisole, levetiracetam, levothyroxine sodium, lidocaine HCl, lincomycin HCl, liothyronine sodium, lisinopril, lomustine (CCNU), lufenuron, lysine, magnesium, mannitol, marbofloxacin, mechlorethamine HCl, meclizine HCl, meclofenamic acid, medetomidine HCl, medium chain triglycerides, medroxyprogesterone acetate, megestrol acetate, melarsomine, melatonin, meloxican, melphalan, meperidine HCl, mercaptopurine, meropenem, metformin HCl, methadone HCl, methazolamide, methenamine mandelate/hippurate, methimazole, methionine, methocarbamol, methohexital sodium, methotrexate, methoxyflurane, methylene blue, methylphenidate, methylprednisolone, metoclopramide HCl, metoprolol, metronidaxole, mexiletine HCl, mibolerlone, midazolam HCl milbemycin oxime, mineral oil, minocycline HCl, misoprostol, mitotane, mitoxantrone HCl, morantel tartrate, morphine sulfate, moxidectin, naloxone HCl, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone HCl, oxytretracycline, oxytocin, pamidronate disodium, pancreplipase, pancuronium bromide, paromomycin sulfate, parozetine HCl, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine HCl, pheylbutazone, phenylephrine HCL, phenypropanolamine HCl, phenyloin sodium, pheromones, parenteral phosphate, phytonadione/vitamin K-1, pimobendan, piperazine, pirlimycin HCL, piroxicam, polysulfated glycosaminoglycan, ponazuril, potassium chloride, pralidoxime chloride, praziquantel, prazosin HCl, prednisolone/prednisone, primidone, procainamide HCl, procarbazine HCl, prochlorperazine, propantheline bromide, *propionibacterium acnes* injection, propofol, propranolol HCl, protamine sulfate, pseudoephedrine HCl, psyllium hydrophilic mucilloid, pyrantel pamoate, pyridostigmine bromide, pyrilamine maleate, pyrimethamine, quinacrine HCl, quinidine, ranitidine HCl, rifampin, s-adenosyl-methionine (SAMe), saline/hyperosmotic laxative, selamectin, selegiline HCL/l-deprenyl, sertraline HCl, sevelamer HCl, sevoflurane, silymarin/milk thistle, sodium bicarbonate, sodium polystyrene sulfonate, sodium stibogluconate, sodium sulfate, sodum thiosulfate, somatotropin, sotalol HCl, spectinomycin HCl, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline HCl, terbutaline sulfate, testosterone, tetracycline HCl, thiabendazole, thiacetarsamide sodium, thiamine HCl, thioguanine, thiopental sodium, thiotepa, thyrotropin, tiamulin, ticarcilin disodium, tiletamine HCl/zolazepam HCl, tilmocsin, tiopronin, tobramycin sulfate, tocamide HCl, tolazoline HCl, telfenamic acid, topiramate, tramadol HCl, trimcinolone acetonide, trientine HCl, trilostane, trimepraxine tartrate w/prednisolone, tripelennamine HCl, tylosin, urdosiol, valproic acid, vanadium, vancomycin HCl, vasopressin, vecuronium bromide, verapamil HCl, vinblastine sulfate, vincristine sulfate, vitamin E/selenium, warfarin sodium, xylazine HCl, yohimbine HCl, zafirlukast, zidovudine (AZT), zinc acetate/zinc sulfate, zonisamide and mixtures thereof.

In one embodiment of the invention, arylpyrazole compounds may be added to the compositions of the invention. Arylpyrazoles may include but are not limited to those described in U.S. Pat. Nos. 6,001,384; 6,010,710; 6,083,519; 6,096,329; 6,174,540; 6,685,954 and 6,998,131, all of which are hereby incorporated by reference in their entirety,—each assigned to Merial, Ltd., Duluth, Ga.).

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962, 499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment of the invention, the class of acaricides or insecticides known as insect growth regulators (IGRs) may also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748, 356; 3,818,047; 4,225,598; 4,798,837; 4,751,225, EP 0 179 022 or U.K. 2 140 010 as well as U.S. Pat. Nos. 6,096,329 and 6,685,954, all of which are hereby incorporated by reference in their entirety, (both assigned to Merial Ltd., Duluth, Ga.). Examples of IGRs suitable for use may include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

An anthelmintic agent that may be combined with the compositions of the invention may be a benzenedisulfonamide compound, which includes but is not limited to clorsulon; or an anti-cestodal agent, which includes but is not limited to praziquantel, pyrantel or morantel.

A parasiticidal agent that may be combined with the compositions of the invention may be a biologically active peptide or protein including, but not limited to, depsipeptides, which act at the neuromuscular junction by stimulating presynaptic receptors belonging to the secretin receptor family resulting in the paralysis and death of parasites. In one embodiment the depsipeptide may be emodepside.

An insecticidal agent that may be combined with the compositions of the invention may be a spinosyn (e.g. spinosad) or a substituted pyridylmethyl derivative compound such as imidacloprid. Agents of this class are described above, and for example, in U.S. Pat. No. 4,742,060 or in EP 0 892 060, both of which are hereby incorporated by reference in their entirety. It would be well within the skill level of the practitioner to decide which individual compound may be used in the inventive formulation to treat a particular infection of an insect. For endoparasites, parasiticides which may be combined include but are not limited to pyrantel, morantel, the benzimidazoles (including albendazole, cambendazole, thiabendazole, fenbendazole, febantel, oxfendazole, oxibendazole, triclabendazole mebendazole and netobimin), levamisole, closantel, rafoxanide, nitroxynil, disophenol and paraherquamide. For ectoparasites, insecticides which may be combined also include but are not limited to pyrethoids, organophosphates and neonicotinoids such as imidacloprid, as well as compounds such as metaflumizone, amitraz and ryanodine receptor antagonists.

Where appropriate, the anthelmintic, parasiticidal and insecticial agent may also be selected from the group of compounds described above as suitable for agrochemical use. In general, the additional pesticidal agent may be included in a dose of between about 0.1 μg and about 10 mg. In one embodiment of the invention, the additional pesticidal agent may be included in a dose of between about 1 μg and about 10 mg. In another embodiment of the invention, the additional pesticidal agent may be included in a dose of about 5 to about 200 μg/kg of weight of animal. In yet another embodiment of the invention, the additional pesticidal agent may be included in a dose between about 0.1 to about 10 mg/kg of weight of animal. In still another embodiment of the invention, the additional pesticidal agent may be included in a dose between about 0.5 to 50 mg/kg.

Certain aspects of the invention are further described by the following paragraphs:
1. A composition for treatment or prophylaxis of parasite infestation in birds or mammals which comprises:
(A) a pharmaceutically effective amount of at least one macrocyclic lactone derivative;
(B) a pharmaceutically effective amount of at least one spirodioxepinoindole derivative or a spirooxepinoindole derivative; and
(C) a pharmaceutically acceptable carrier.
2. A composition according to paragraph 1, wherein the macrocyclic lactone derivative is an avermectin or milbemycin derivative.
3. A composition according to paragraphs 1 or 2, wherein the macrocyclic lactone derivative is ivermectin.
4. A composition according to any of paragraphs 1-3, wherein the macrocyclic lactone derivative is abamectin.
5. A composition according to paragraphs 1-4, wherein the macrocyclic lactone derivative is moxidectin.
6. A composition according to paragraphs 1 or 2, wherein the macrocyclic lactone derivative is a compound of formula (II):

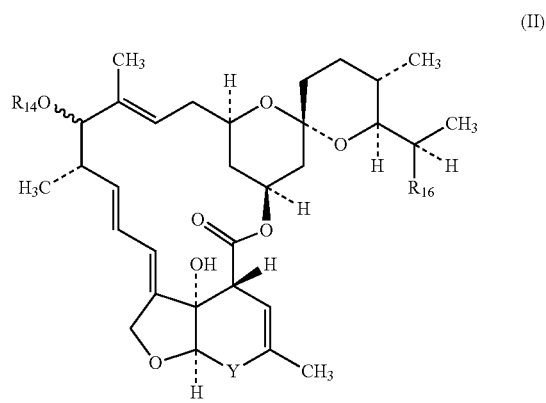

wherein:
$R_{14}$ represents —$(CH_2)_s$—O—Z
wherein,
s is 1 or 2;
Y represents —$CH(OR_{15})$—, —$C(=O)$— or —$C(=NOR_{15})$;
$R_{15}$ represents hydrogen, alkyl or phenyl;
$R_{16}$ represents —$CH_3$ or —$CH_2CH_3$; and
Z is a mono- or disaccharide group, alkyl, alkenyl, alkynyl, acyl, alkylalkoxy, aryl, alkanoyloxy, alkoxycarbonyl, alkenoyl, alkynoyl, or aroyl.
7. A composition according to any of paragraphs 1, 2 or 6, wherein the macrocyclic lactone derivative is a compound of formula (IIa):

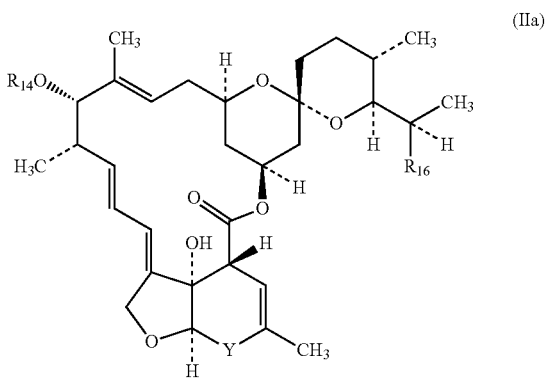

wherein:
$R_{14}$ represents —$(CH_2)_s$—O—Z
wherein,
s is 1 or 2;
Y represents —$CH(OR_{15})$—, —$C(=O)$— or —$C(=NOR_{15})$;
$R_{15}$ represents hydrogen, $C_1$-$C_4$ alkyl or phenyl;
$R_{16}$ represents —$CH_3$ or —$CH_2CH_3$; and Z is a mono- or disaccharide group, alkyl, alkenyl, alkynyl, acyl, alkylalkoxy, aryl, alkanoyloxy, alkoxycarbonyl, alkenoyl, alkynoyl, or aroyl.

8. A composition according to paragraphs 1, 2 or 6, wherein the macrocyclic lactone derivative is a compound of formula (III):

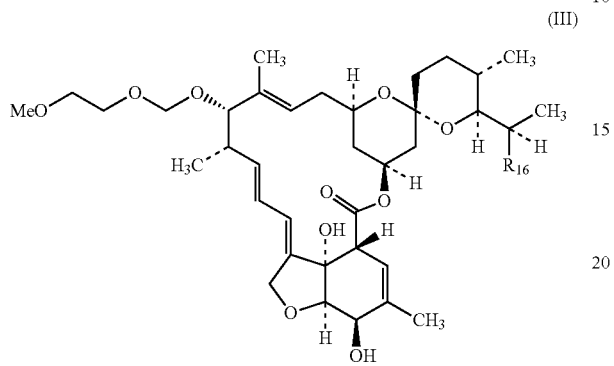

(III)

wherein:

$R_{16}$ represents —CH$_3$ or —CH$_2$CH$_3$.

9. A composition according to paragraphs 1, 2 or 6, wherein the macrocyclic lactone derivative is a compound of formula (IIb):

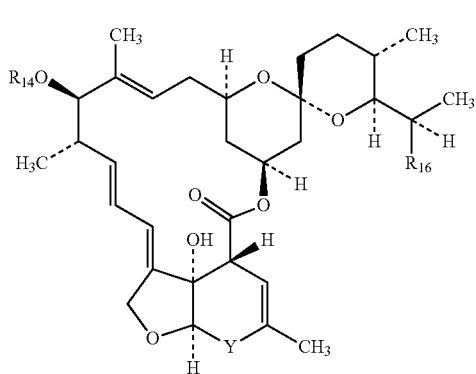

(IIb)

wherein:

$R_{14}$ represents —(CH$_2$)$_s$—O—Z wherein, s is 1 or 2;

Y represents —CH(OR$_{15}$)—, —C(=O)— or —C(=NOR$_{15}$);

$R_{15}$ represents hydrogen, $C_1$-$C_4$ alkyl or phenyl;

$R_{16}$ represents —CH$_3$ or —CH$_2$CH$_3$; and

Z is a mono- or disaccharide group, alkyl, alkenyl, alkynyl, acyl, alkylalkoxy, aryl, alkanoyloxy, alkoxycarbonyl, alkenoyl, alkynoyl, or aroyl.

10. A composition according to paragraphs 1, 2 or 6, wherein the macrocyclic lactone derivative is a compound of formula (IV):

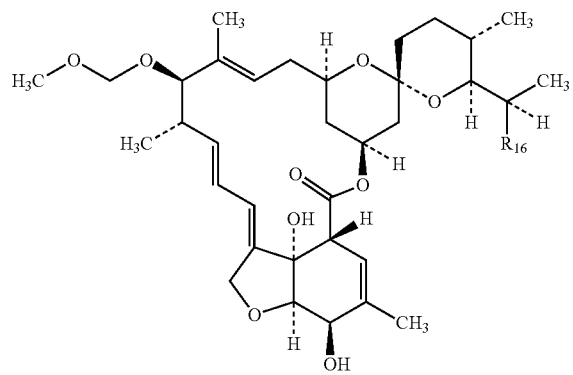

(IV)

wherein:

$R_{16}$ represents —CH$_3$ or —CH$_2$CH$_3$.

11. A composition according to any of paragraphs 1-10, wherein the spirodioxepinoindole derivative is a paraherquamide.

12. A composition according to any of paragraphs 1-10, wherein the spirodioxepinoindole derivative is a deoxyparaherquamide.

13. A composition according to any of paragraphs 1-10, wherein the spirodioxepinoindole derivative is a macfortine.

14. The composition of any of paragraphs 1-13, which further comprises at least one additional macrocyclic lactone compound.

15. The composition of any of paragraphs 1-14, which further comprises an anti-cestodal agent.

16. The composition of paragraph 15, wherein the one additional macrocyclic lactone compound is eprinomectin and the cestodal agent is praziquantel.

17. The composition of any of paragraphs 1-16, which further comprises a nitroguanidine or pyridylmethylamine insecticide.

18. The composition of paragraph 17, wherein the nitroguanidine or pyridylmethylamine insecticide is imidacloprid.

19. A method for the treatment or prophylaxis of a parasitic infestation in a bird or mammal which comprises administering a pharmaceutically effective amount of the composition of any of paragraphs 1-18.

20. The method of paragraph 19, wherein the composition is in the form selected from the group consisting of a ready-to-use formulation, pour-on formulation, a spot-on formulation, paste formulation, oral drench formulation, capsule formulation, 3-way drench formulation, transdermal or transmucosal formulation, chewable formulation and injectable formulation.

21. The method of paragraphs 19 or 20, wherein the mammal is a bovine.

EXAMPLES

The following examples are provided to illustrate certain embodiments of the invention and are not to be construed in any way as limiting the scope of the invention.

Equine Paste Formulation

Paste formulations comprising at least one macrocyclic lactone, 2-desoxoparaherquamide and optionally other anthelmintics such as praziquantel are prepared using approximately the following amounts of the two active agents and the excipients listed. The paste formulations are suitable for administration to equines and other animals.
2-desoxoparaherquamide 40 mg/mL 2.0 mg/Kg body weight
Macrocyclic lactone 4 mg/mL 0.2 mg/Kg body weight
Dose volume=1 ml/20 kg

| Raw Material | Approx. % w/v |
|---|---|
| Benzyl Alcohol | 5.00 to 10.00 |
| Absolute Alcohol | 1.00 to 3.00 |
| Abamectin | 0.40 |
| 2-desoxoparaherquamide | 4.00 |
| Polysorbate | 1.00 to 2.00 |
| Silicon dioxide | 4.00 to 6.00 |
| Microcrystalline cellulose | 0.5 to 3.00 |
| Crodamol ® | to 100% |

| Ingredient | Approx. % w/w |
|---|---|
| Doramectin | 0.40 |
| 2-desoxoparaherquamide | 4.00 |
| Benzyl Alcohol | 5.00 to 15.00 |
| Absolute Alcohol | 1.00 to 3.00 |
| Polysorbate | 1.00 to 2.00 |
| Silicon dioxide | 4.00 to 6.00 |
| Microcrystalline cellulose | 0.5 to 3.00 |
| Crodamol ® | to 100% |

| Ingredient | Approx. % w/w |
|---|---|
| Ivermectin | 0.40 |
| 2-desoxoparaherquamide | 4.00 |
| Benzyl Alcohol | 5.00 to 15.00 |
| Absolute Alcohol | 1.00 to 3.00 |
| Polysorbate | 1.00 to 2.00 |
| Silicon dioxide | 4.00 to 6.00 |
| Microcrystalline cellulose | 0.5 to 3.00 |
| Crodamol ® | to 100% |

An example of the formulation in which praziquantel is additionally included is as follows:

| Ingredient | Approx. % w/w |
|---|---|
| Ivermectin | 0.40 |
| 2-desoxoparaherquamide | 4.00 |
| Praziquantel | 5.00 |
| Benzyl Alcohol | 5.00 to 15.00 |
| Absolute Alcohol | 1.00 to 3.00 |
| Polysorbate | 1.00 to 2.00 |
| Silicon dioxide | 4.00 to 6.00 |
| Microcrystalline cellulose | 0.5 to 3.00 |
| Crodamol ® | to 100% |

Two Way Drench

A two way drench formulation comprising a macrocyclic lactone and 2-desoxoparaherquamide and optionally other anthelmintic agents such as praziquantel or triclabendazole is prepared with the components listed in the table below. These formulations would be suitable for administration to sheep or cattle.
2-desoxoparaherquamide 10 mg/mL, 2.0 mg/Kg body weight
Macrocyclic lactone 1 mg/mL 0.2 mg/Kg body weight
Dose volume=1 mL/5 kg Formulation suitable for controlling gastrointestinal roundworms, lungworm; including macrocyclic lactone, benzimidazole, levamisole/morantel resistant strains.

| Raw Material | Approx. % w/v |
|---|---|
| Ivermectin | 0.10 |
| 2-desoxoparaherquamide | 1.0 |
| Water | 1.00 to 3.00 |
| Propylene Glycol | to 100% |

| Ingredient | Approx. % w/v |
|---|---|
| Ivermectin | 0.1 |
| 2-desoxoparaherquamide | 1 |
| Benzyl Alcohol | 2-5 |
| Polysorbate 80 | 10 |
| Propylene Glycol | 20 |
| Sod.dihyd.phos.dihydrate | 1-2 |
| Disod.phos.dihydrate | 0.1 |
| Glycerol formal | 10 |
| Purified water | To 100 |

| Ingredient | Approx. % w/v |
|---|---|
| Moxidectin | 0.1 |
| 2-desoxoparaherquamide | 1 |
| Benzyl Alcohol | 2-5 |
| EDTA | 0.05 |
| Sod.dihyd.phos.dihydrate | 1-2 |
| Disod.phos.dihydrate | 0.1 |
| Purified water | 10 |
| Propylene glycol | To 100 |

2-desoxoparaherquamide 10 mg/mL, 2.0 mg/Kg bwt
Macrocyclic lactone 1 mg/mL 0.2 mg/Kg bwt
Praziquantel 18.8 mg/mL, 3.76 mg/kg
Dose volume=1 mL/5 kg Formulation suitable for controlling gastrointestinal roundworms, lungworm; including macrocyclic lactone, benzimidazole, levamisole/morantel resistant strains. Also control of praqziquantel sensitive tapeworm strains.

| Ingredient | Approx. % w/v |
|---|---|
| Ivermectin | 0.1 |
| 2-desoxoparaherquamide | 1.0 |
| Praziquantel | 1.88 |
| PEG 8000 | 2-5 |
| Benzyl Alcohol | 2-5 |
| Polysorbate 80 | 10 |
| Propylene Glycol | 20 |
| Sod.dihyd.phos.dihydrate | 1-2 |
| Disod.phos.dihydrate | 0.1 |
| Glycerol formal | 10 |
| Xanthan gum | 0.2-0.5 |
| Aerosil 200 | 1 |
| Purified water | To 100 |

2-desoxoparaherquamide 10 mg/mL, 2.0 mg/Kg bwt
Macrocyclic lactone 1 mg/mL 0.2 mg/Kg bwt
Triclabendazole 50 mg/mL, 5.0 mg/kg
Dose volume=1 mL/5 kg Formulation suitable for controlling gastrointestinal roundworms, lungworm; including macrocyclic lactone, benzimidazole, levamisole/morantel resistant strains. Also control of triclabendazole sensitive liver fluke strains.

| Ingredient | Approx. % w/v |
| --- | --- |
| Moxidectin | 0.1 |
| 2-desoxoparaherquamide | 1.00 |
| Triclabendazole | 5.00 |
| PEG 8000 | 2-5 |
| Benzyl Alcohol | 2-5 |
| Polysorbate 80 | 10 |
| Propylene Glycol | 20 |
| Sod.dihyd.phos.dihydrate | 1-2 |
| Disod.phos.dihydrate | 0.1 |
| Glycerol formal | 10 |
| Xanthan gum | 0.2-0.5 |
| Aerosil 200 | 1 |
| Purified water | To 100 |

Sustained Release Capsule

A capsule or tablet for sustained release comprising a macrocyclic lactone and 2-desoxoparaherquamide is prepared using the components listed in the following table according to the methods described in U.S. Pat. Nos. 4,687,480 or 4,671,789, which are incorporated herein by reference in their entirety. The formulations are suitable for administration to cattle and sheep.

The formulations are suitable for controlling gastrointestinal roundworms and lungworm, including strains resistant to macrocyclic lactones, benzimidazole and levamisole/morantel.

Number and size of tablets determine dose and payout period.

| Component | Approx. % w/w |
| --- | --- |
| Ivermectin | 1.35 |
| 2-desoxoparaherquamide | 13.5 |
| Lactose/Sugar Ester | 60.00 to 80.00 |
| PVP | 0.50 to 1.50 |
| Magnesium Stearate | 0.10 to 0.30 |
| Water | to 100% |

| Component | Approx. % w/w |
| --- | --- |
| Doramectin | 1.35 |
| 2-desoxoparaherquamide | 13.5 |
| Lactose/Sugar Ester | 60.00 to 80.00 |
| PVP | 0.50 to 1.50 |
| Magnesium Stearate | 0.10 to 0.30 |
| Water | to 100% |

4Way Drench

An oral drench in which 3 or 4 anthelmintics are included is prepared with the components listed in the table below. This could be prepared in the manner described in U.S. Patent Publication No. 2006/0198850, which is incorporated herein by reference in its entirety.

2-desoxoparaherquamide 10 mg/mL, 2.0 mg/Kg bwt

Abamectin 1 mg/mL, 0.2 mg/Kg bwt

Levamisole 40 mg/mL,

Albendazole 23.8 mg/mL,

Dose volume=1 mL/5 kg

The formulations are suitable for controlling gastrointestinal roundworms, lungworm; including macrocyclic lactone, benzimidazole, levamisole/morantel resistant strains.

| Raw Material | % w/v |
| --- | --- |
| Levamisole Hydrochloride | 4.0 |
| Albendazole | 2.38 |
| Defoamer | 2.00 |
| 2-desoxoparaherquamide | 1.0 |
| Abamectin | 0.1 |
| Capmul MCM | 1.10 |
| Aerosil | 1.30 |
| Xanthan Gum | 0.38 |
| Propylene Glycol | 0.75 |
| Water | to 100% |

| Component | Approx. % w/v |
| --- | --- |
| Levamisole Hydrochloride | 4.0 |
| Albendazole | 2.38 |
| 2-desoxoparaherquamide | 1.0 |
| Ivermectin | 0.1 |
| Defoamer | 2.00 |
| Capmul MCM or Miglyol 840 | 1.0-5.00 |
| Aerosil | 1.0-2.00 |
| Xanthan Gum | 0-1.00 |
| Propylene Glycol | 0.5-2.00 |
| Water | to 100% |

Pour On

Pour-On formulations suitable for topical administration to cattle containing a macrocyclic lactone active and 2-desoxyparaherquamide. The manner of preparation of these formulations would be that both the macrocyclic lactone active and 2-desoxyparaherquamide would be dissolved in an organic solvent such as benzyl alcohol, propylene dicaprate/dicaprylate, glycerol formal, n-methylpyrrolidone. The organic solvent could then be mixed with a co-solvent or oil carrier.

2-desoxyparaherquamide 1000 mg/mL, 5 mg/kg

Macrocyclic lactone 100 mg/mL, 500 mcg/kg

Dose volume=1 ml per 20 kg

Formulation suitable for controlling gastrointestinal roundworms, lungworm; including macrocyclic lactone, benzimidazole, levamisole/morantel resistant strains.

| Material | Approx. % w/v |
| --- | --- |
| Abamectin | 1.0 |
| 2-desoxoparaherquamide | 10.0 |
| Benzyl Alcohol | 20.0 |
| Soybean Oil | to 100% |

| Component | Approx. % w/v |
| --- | --- |
| Ivermectin | 1.0 |
| 2-desoxoparaherquamide | 10.0 |
| Benzyl Alcohol | 10.0-20.0 |
| Soybean Oil | to 100% |

| Component | Approx. % w/v |
| --- | --- |
| Doramectin | 1.0 |
| 2-desoxoparaherquamide | 10.0 |
| Benzyl Alcohol | 10.0-20.0 |
| Soybean Oil | to 100% |

2-desoxyparaherquamide 500 mg/mL, 5 mg per kg

Macrocyclic lactone 50 mg/mL, 500 mcg/kg

Dose volume=1 ml perl Okg

Formulation suitable for controlling gastrointestinal roundworms, lungworm; including macrocyclic lactone, benzimidazole, levamisole/morantel resistant strains.

| Component | Approx. % w/v |
| --- | --- |
| Eprinomectin | 0.5% |
| 2-desoxoparaherquamide | 5.0% |
| Propylene dicaprate/dicaprylate | to 100% |

| Component | Approx. % w/v |
| --- | --- |
| Moxidectin | 0.5% |
| 2-desoxoparaherquamide | 5.0% |
| Propylene dicaprate/dicaprylate | to 100% |

All formulations may include optional antioxidants (BHA/BHT), buffering agents and added trace elements, vitamins, minerals and the like.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A composition for the treatment of parasite infestation or infection in a ruminant animal which comprises:
    (a) a pharmaceutically effective amount of at least one macrocyclic lactone derivative wherein the macrocyclic lactone derivative is ivermectin, doramectin, eprimomectin or moxidectin;
    (b) a pharmaceutically effective amount of at least one paraherquamide or macfortine;
    (c) a further anthelmintic agent selected from praziquantel, pyrantel, and morantel; and
    (d) a pharmaceutically acceptable carrier.

2. The composition according to claim 1, wherein the composition comprises a deoxyparaherquamide.

3. The composition according to claim 1, which further comprises at least one additional macrocyclic lactone compound.

4. A method for the treatment of a parasitic infestation or infection in a ruminant animal which comprises administering a pharmaceutically effective amount of the composition of claim 1 to the ruminant animal.

5. The method of claim 4, wherein the ruminant animal is a bovine.

6. The composition of claim 1, wherein the composition is in the form of a paste formulation, an oral drench formulation, a capsule formulation, a chewable formulation, a sustained-release tablet, or a premix formulation.

7. The composition of claim 1, wherein the composition is in the form of a sustained-release capsule for insertion in the rumen of a ruminant animal.

8. The composition according to claim 1, wherein the macrocyclic lactone derivative is doramectin.

9. The composition according to claim 1, wherein the macrocyclic lactone derivative is moxidectin.

10. The composition according to claim 1, wherein the macrocyclic lactone derivative is ivermectin or eprinomectin.

11. The composition according to claim 3, wherein the at least one additional macrocyclic lactone compound is eprinomectin and the further anthelmintic agent is praziquantel.

12. A composition for the treatment of parasite infestation or infection in a ruminant animal, the composition comprising:
    (a) a pharmaceutically effective amount of a milbemycin selected from the group consisting of milbemectin, milbemycin D, nemadectin, and combinations thereof;
    (b) a pharmaceutically effective amount of at least one spirodioxepinoindole derivative or a spirooxepinoindole derivative;
    (c) a further anthelmintic agent selected from praziquantel, pyrantel, and morantel; and
    (d) a pharmaceutically acceptable carrier.

13. The composition according to claim 12, wherein the spirodioxepinoindole derivative is a paraherquamide.

14. The composition according to claim 12, wherein the spirodioxepinoindole derivative is a deoxyparaherquamide.

15. The composition according to claim 12, wherein the spirodioxepinoindole derivative is a macfortine.

16. The composition according to claim 12, which further comprises at least one additional macrocyclic lactone compound.

17. The composition according to claim 16, wherein the at least one additional macrocyclic lactone compound is eprinomectin and the further anthelmintic agent is praziquantel.

18. The composition of claim 12, wherein the composition is in the form of a paste formulation, an oral drench formulation, a capsule formulation, a chewable formulation, a sustained-release tablet, or a premix formulation.

19. The composition of claim 12, wherein the composition is in the form of a sustained-release capsule for insertion in the rumen of a ruminant animal.

* * * * *